United States Patent
Kitagawa et al.

(10) Patent No.: US 8,808,749 B2
(45) Date of Patent: Aug. 19, 2014

(54) POLYMER CONJUGATE OF BIOACTIVE SUBSTANCE HAVING HYDROXY GROUP

(75) Inventors: Masayuki Kitagawa, Tokyo (JP); Chieko Seno, Tokyo (JP); Keiko Ebara, Tokyo (JP); Kazutoshi Takashio, Tokyo (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/319,175

(22) PCT Filed: May 12, 2010

(86) PCT No.: PCT/JP2010/058034
§ 371 (c)(1),
(2), (4) Date: Jan. 13, 2012

(87) PCT Pub. No.: WO2010/131675
PCT Pub. Date: Nov. 18, 2010

(65) Prior Publication Data
US 2012/0116051 A1    May 10, 2012

(30) Foreign Application Priority Data
May 15, 2009   (JP) ................. 2009-118365

(51) Int. Cl.
| | | |
|---|---|---|
| A61K 9/14 | (2006.01) |
| A61K 31/365 | (2006.01) |
| A61K 31/19 | (2006.01) |
| A61K 31/195 | (2006.01) |
| A61K 31/337 | (2006.01) |
| C08G 69/10 | (2006.01) |
| A61K 47/48 | (2006.01) |
| A61K 31/167 | (2006.01) |
| C08G 69/48 | (2006.01) |
| A61K 31/573 | (2006.01) |
| A61K 31/7068 | (2006.01) |
| A61K 31/704 | (2006.01) |
| A61K 31/52 | (2006.01) |
| C08G 69/40 | (2006.01) |
| A61K 31/4745 | (2006.01) |
| A61K 31/7052 | (2006.01) |

(52) U.S. Cl.
CPC .............. *C08G 69/10* (2013.01); *A61K 31/365* (2013.01); *A61K 31/19* (2013.01); *A61K 31/195* (2013.01); *A61K 31/337* (2013.01); *A61K 47/48315* (2013.01); *A61K 31/167* (2013.01); *C08G 69/48* (2013.01); *A61K 31/573* (2013.01); *A61K 31/7068* (2013.01); *A61K 31/704* (2013.01); *A61K 31/52* (2013.01); *C08G 69/40* (2013.01); *A61K 31/4745* (2013.01); *A61K 47/48215* (2013.01); *A61K 31/7052* (2013.01)
USPC ........................................................ 424/489

(58) Field of Classification Search
None
See application file for complete search history.

(56) References Cited

U.S. PATENT DOCUMENTS

| | | |
|---|---|---|
| 3,979,449 A | 9/1976 | Hirsbrunner et al. |
| 4,734,512 A | 3/1988 | Kaneko et al. |
| 4,892,733 A | 1/1990 | Bichon et al. |
| 5,037,883 A | 8/1991 | Kopecek et al. |
| 5,182,203 A | 1/1993 | Ebersole et al. |
| 5,412,072 A | 5/1995 | Sakurai et al. |
| 5,438,072 A | 8/1995 | Bobee et al. |
| 5,510,103 A | 4/1996 | Yokoyama et al. |
| 5,552,517 A | 9/1996 | Martin |
| 5,571,889 A | 11/1996 | Katoh et al. |
| 5,614,549 A | 3/1997 | Greenwald et al. |
| 5,639,832 A | 6/1997 | Kroner et al. |
| 5,693,751 A | 12/1997 | Sakurai et al. |
| 5,877,205 A | 3/1999 | Andersson |
| 5,985,548 A | 11/1999 | Collier et al. |
| 6,025,385 A | 2/2000 | Shimizu et al. |
| 6,153,655 A | 11/2000 | Martinez et al. |
| 6,262,107 B1 | 7/2001 | Li et al. |
| 6,322,817 B1 | 11/2001 | Maitra et al. |
| 6,376,470 B1 | 4/2002 | Greenwald et al. |
| 6,410,731 B2 | 6/2002 | Curran et al. |

| | | | | | | |
|---|---|---|---|---|---|---|
| 6,458,347 B1 * | 10/2002 | Sugawara et al. ........ 424/78.17 | JP | 63-502037 A | 8/1988 | |
| 6,573,284 B1 | 6/2003 | Riley et al. | JP | 64-61422 A | 3/1989 | |
| 6,596,757 B1 | 7/2003 | Chari et al. | JP | 64-61423 A | 3/1989 | |
| 6,713,454 B1 | 3/2004 | Ekwuribe et al. | JP | 2-300133 A | 12/1990 | |
| 6,720,304 B1 | 4/2004 | Sinn et al. | JP | 5-955 A | 1/1993 | |
| 6,720,306 B2 | 4/2004 | Greenwald et al. | JP | 5-117385 A | 5/1993 | |
| 6,858,582 B2 | 2/2005 | Yatvin et al. | JP | 6-107565 A | 4/1994 | |
| 7,138,490 B2 | 11/2006 | Nakanishi et al. | JP | 6-206815 A | 7/1994 | |
| 7,176,185 B2 | 2/2007 | Hilfinger et al. | JP | 6-206830 A | 7/1994 | |
| 7,495,099 B2 | 2/2009 | Kitagawa et al. | JP | 6-206832 A | 7/1994 | |
| 7,700,709 B2 | 4/2010 | Masuda et al. | JP | 6-329085 A | 11/1994 | |
| 7,820,759 B2 | 10/2010 | Shimizu et al. | JP | 8-48766 A | 2/1996 | |
| 8,188,222 B2 | 5/2012 | Yamamoto et al. | JP | 8-503689 H | 4/1996 | |
| 8,323,669 B2 | 12/2012 | Kitagawa et al. | JP | 8-507558 A | 8/1996 | |
| 8,334,364 B2 | 12/2012 | Yamamoto et al. | JP | 8-310970 A | 11/1996 | |
| 8,703,878 B2 | 4/2014 | Kitagawa et al. | JP | 2694923 B2 | 12/1997 | |
| 2001/0003779 A1 | 6/2001 | Curran et al. | JP | 10-513187 H | 12/1998 | |
| 2001/0014354 A1 | 8/2001 | Yokoyama et al. | JP | 11-335267 A | 12/1999 | |
| 2001/0041189 A1 | 11/2001 | Xu | JP | 2000-515132 A | 11/2000 | |
| 2002/0009426 A1 | 1/2002 | Greenwald et al. | JP | 2000-517304 A | 11/2000 | |
| 2002/0016285 A1 | 2/2002 | Bhatt et al. | JP | 2000-516948 A | 12/2000 | |
| 2002/0099013 A1 | 7/2002 | Piccariello et al. | JP | 2001-226294 A | 8/2001 | |
| 2002/0119951 A1 | 8/2002 | Seyedi et al. | JP | 2002-69184 A | 3/2002 | |
| 2002/0161062 A1 | 10/2002 | Biermann et al. | JP | 2002-508400 A | 3/2002 | |
| 2002/0183259 A1 | 12/2002 | Choe et al. | JP | 3268913 B2 | 3/2002 | |
| 2003/0032593 A1 | 2/2003 | Wender et al. | JP | 2002-512265 A | 4/2002 | |
| 2003/0054977 A1 | 3/2003 | Kumar et al. | JP | 3310000 B2 | 7/2002 | |
| 2003/0149003 A1 | 8/2003 | Chaplin et al. | JP | 2003-509385 A | 3/2003 | |
| 2005/0054026 A1 | 3/2005 | Atsushi et al. | JP | 2003-509386 A | 3/2003 | |
| 2005/0119193 A1 | 6/2005 | Motoyama | JP | 2003-511349 A | 3/2003 | |
| 2005/0147617 A1 | 7/2005 | Ji et al. | JP | 2003-511423 A | 3/2003 | |
| 2005/0171036 A1 | 8/2005 | Arakawa et al. | JP | 2003-524028 A | 8/2003 | |
| 2006/0009622 A1 | 1/2006 | Fuselier et al. | JP | 2003-525238 A | 8/2003 | |
| 2006/0057219 A1 | 3/2006 | Nagasaki et al. | JP | 2003-527443 A | 9/2003 | |
| 2006/0067910 A1 | 3/2006 | Kitagawa et al. | JP | 2003-342167 A | 12/2003 | |
| 2006/0099265 A1 | 5/2006 | Shimizu et al. | JP | 2003-342168 A | 12/2003 | |
| 2006/0233883 A1 | 10/2006 | Ishihara et al. | JP | 2003-342269 A | 12/2003 | |
| 2006/0258569 A1 | 11/2006 | McTavish | JP | 2004-530736 A | 10/2004 | |
| 2007/0004674 A1 | 1/2007 | Shiotsu et al. | JP | 2004-532289 A | 10/2004 | |
| 2007/0196497 A1 | 8/2007 | Pouliquen et al. | JP | 2005-507912 A | 3/2005 | |
| 2008/0113028 A1 | 5/2008 | Shimizu et al. | JP | 2005-508832 A | 4/2005 | |
| 2008/0145432 A1 | 6/2008 | Kakizawa et al. | JP | 2005-517675 A | 6/2005 | |
| 2008/0221062 A1 | 9/2008 | Miyamoto et al. | JP | 2005-519122 A | 6/2005 | |
| 2008/0269218 A1 | 10/2008 | Kuramochi et al. | JP | 2005-533026 A | 11/2005 | |
| 2008/0280937 A1 | 11/2008 | Leamon et al. | JP | 2006-510627 A | 3/2006 | |
| 2009/0012252 A1 | 1/2009 | Masuda et al. | JP | 2006-511571 A | 4/2006 | |
| 2009/0156742 A1 | 6/2009 | Shimizu et al. | JP | 2006-517572 A | 7/2006 | |
| 2009/0162313 A1 | 6/2009 | Kitagawa et al. | JP | 2006-521367 A | 9/2006 | |
| 2009/0239782 A1 | 9/2009 | Nakamura et al. | JP | 2006-524673 A | 11/2006 | |
| 2009/0275732 A1 | 11/2009 | Hirotsu et al. | JP | 2007-511586 A | 5/2007 | |
| 2009/0281300 A1 | 11/2009 | Yamamoto et al. | JP | 2007-191643 A | 8/2007 | |
| 2010/0004403 A1 * | 1/2010 | Kitagawa et al. ............ 525/408 | WO | 93/24476 A1 | 12/1993 | |
| 2010/0029234 A1 | 2/2010 | Yamamoto et al. | WO | 96/23794 A1 | 8/1996 | |
| 2010/0234537 A1 | 9/2010 | Kitagawa et al. | WO | 97/38727 A1 | 10/1997 | |
| 2010/0292414 A1 | 11/2010 | Kitagawa et al. | WO | 98/02426 A1 | 1/1998 | |
| 2011/0136990 A1 | 6/2011 | Harada et al. | WO | 98/07713 A1 | 2/1998 | |
| 2011/0201754 A1 | 8/2011 | Kitagawa et al. | WO | 98/08489 A1 | 3/1998 | |
| 2011/0294980 A1 | 12/2011 | Nakanishi et al. | WO | 99/30727 A1 | 6/1999 | |
| 2013/0331517 A1 | 12/2013 | Yamamoto et al. | WO | 99/53951 A1 | 10/1999 | |
| 2014/0024703 A1 | 1/2014 | Shimizu et al. | WO | 01/19361 A2 | 3/2001 | |
| | | | WO | 01/19406 A2 | 3/2001 | |
| | | | WO | 01/19407 A2 | 3/2001 | |
| FOREIGN PATENT DOCUMENTS | | | WO | 01/26693 A2 | 4/2001 | |
| | | | WO | 01/64198 A2 | 9/2001 | |
| CA | 2383240 A1 | 3/2001 | WO | 01/70275 A2 | 9/2001 | |
| CA | 2334615 A1 | 8/2001 | WO | 01/92584 A1 | 12/2001 | |
| CN | 1307866 A | 8/2001 | WO | 02/06279 A1 | 1/2002 | |
| CN | 1708540 A | 12/2005 | WO | 02/065986 A2 | 8/2002 | |
| CN | 1800238 A | 7/2006 | WO | 02/065988 A2 | 8/2002 | |
| EP | 0397307 A2 | 11/1990 | WO | 02/066066 A1 | 8/2002 | |
| EP | 0583955 A2 | 2/1994 | WO | 03/000771 A1 | 1/2003 | |
| EP | 0757049 A1 | 2/1997 | WO | 03/035008 A2 | 5/2003 | |
| EP | 1127570 A2 | 8/2001 | WO | 03/055860 A1 | 7/2003 | |
| EP | 1580216 A1 | 9/2005 | WO | 2004/039869 A1 | 5/2004 | |
| EP | 1857446 A1 | 11/2007 | WO | 2004/050087 A1 | 6/2004 | |
| JP | 61-243026 A | 10/1986 | WO | 2004/056782 A1 | 7/2004 | |
| JP | 62-96088 A | 5/1987 | WO | 2004/072051 A1 | 8/2004 | |
| JP | 62-145093 A | 6/1987 | WO | 2004/082718 A1 | 9/2004 | |
| JP | 63-10789 A | 1/1988 | WO | 2004/096212 A1 | 11/2004 | |
| JP | 63-23884 A | 2/1988 | | | | |

| | | |
|---|---|---|
| WO | 2005/000300 A1 | 1/2005 |
| WO | 2005/018674 A1 | 3/2005 |
| WO | 2005/066214 A1 | 7/2005 |
| WO | 2006/033296 A1 | 3/2006 |
| WO | 2006/055670 A2 | 5/2006 |
| WO | 2006/055760 A1 | 5/2006 |
| WO | 2006/095668 A1 | 9/2006 |
| WO | 2006/095783 A1 | 9/2006 |
| WO | 2006/101052 A1 | 9/2006 |
| WO | 2006/115293 A1 | 11/2006 |
| WO | 2006/120914 A | 11/2006 |
| WO | 2007/022493 A2 | 2/2007 |
| WO | 2007/080898 A1 | 7/2007 |
| WO | 2007/111211 A1 | 10/2007 |
| WO | 2007/135910 A1 | 11/2007 |
| WO | 2008/010463 A1 | 1/2008 |
| WO | 2008/041610 A1 | 4/2008 |
| WO | 2008/056596 A1 | 5/2008 |
| WO | 2008/056654 A1 | 5/2008 |
| WO | 2009/041570 A1 | 4/2009 |
| WO | 2009/116509 A1 | 9/2009 |
| WO | 2009/142326 A1 | 11/2009 |

OTHER PUBLICATIONS

Final Rejection mailed Oct. 17, 2012 in co-pending U.S. Appl. No. 12/678,620.
International Search Report dated Jan. 29, 2008 in co-pending international patent application No. PCT/JP2007/071532.
International Search Report dated Dec. 9, 2008 in co-pending international patent application No. PCT/JP2008/067413.
Office Action dated Jan. 21, 2009 in co-pending U.S. Appl. No. 10/548,998.
Office Action dated Apr. 17, 2009 in co-pending U.S. Appl. No. 10/548,998.
Office Action dated Jul. 10, 2009 in co-pending U.S. Appl. No. 10/548,998.
Final Rejection dated Mar. 4, 2010 in co-pending U.S. Appl. No. 10/548,998.
Office Action dated Aug. 24, 2010 in co-pending U.S. Appl. No. 11/662,834.
Office Action dated Nov. 12, 2010 in co-pending U.S. Appl. No. 11/662,834.
Final Rejection dated Jun. 8, 2011 in co-pending U.S. Appl. No. 11/662,834.
Office Action dated Jun. 16, 2011 in co-pending U.S. Appl. No. 12/225,230.
Office Action dated Sep. 9, 2011 in co-pending U.S. Appl. No. 12/226,962.
Office Action dated Jul. 21, 2010 in abandoned U.S. Appl. No. 12/309,061.
Final Rejection dated Feb. 28, 2011 in abandoned U.S. Appl. No. 12/309,061.
Office Action dated Apr. 4, 2011 in co-pending U.S. Appl. No. 12/311,086.
Final Rejection dated Jul. 27, 2011 in co-pending U.S. Appl. No. 12/311,086.
Course for Universities, Third Edition, Revised and supplemented, "Visshaja Shkola" Publishing House, 1981, 656 pages, see p. 265, "High-Molecular Weight Compounds", Shur.
6001 Chemical Abstracts, American Chemical Society, US, vol. 132, No. 2, Oct. 1, 2000, XP-002168038, 1 page abstract, "Polymer Micelle Compositions Containing Poorly Water-Soluble Drugs and their Preparation", Ichiro, et al.
Merriam-Webster's Collegiate Dictionary—11th Edition, 2004, 22 pages.
J. Org. Chem 2001, 66, 8135-8138, "Novel Syntheses of Cis and Trans Isomers of Combretastatin A-4", Gaukroger, et al.
Anti Cancer Drug Design, vol. 14, No. 6, Dec. 1999, ISSN 0266-9536, pp. 539-548, "Synthesis and antitumor activities of amino acid prodrugs of amino-combretastatins", Ohsumi, et al.
Journal of Pharmaceutical Sciences, vol. 92, No. 7, Jul. 2003, pp. 1343-1355, "MiniReview-Amphiphilic Block Copolymers for Drug Delivery", Adams, et al.

Chemistry and Biology, vol. 11, 787-797, Jun. 2004, "Targeting Wide-Range Oncogenic Transformation via PU24FCI, a Specific Inhibitor of Tumor Hsp90", Vilenchik, et al.
Trends in Molecular Medicine, vol. 8, No. 4, (Supp.) 2002, p. S55-61, "Hsp90 Inhibitors as Novel Cancer Chemotherapeutic Agents", Neckers, et al.
Current Cancer Drug Targets, 2003, vol. 3, 385-390, "The Clinical Applications of Heat Shock Protein Inhibitors in Cancer—Present and Future", Banerji, et al.
Cancer Science, Feb. 2004, V. 95, No. 2, 105-111, "Antitumor Activity of Sugar-Modified Cytosine Nucleosides", Matsuda, et al.
Cancer Research vol. 44, Jan. 25-30, 1984, "Antitumor Activity of 1-B-D-Arabinofuranosylcytosine Conjugated with Polyglutamic Acid and its Derivative", Kato, et al.
Journal of Controlled Release vol. 79 (2002), 55-70, "Anticancer Drug Delivery Systems: Multi-Loaded N4-acyl poly (ethylene glycol) prodrugs of ara-C. II. Efficacy in ascites and solid tumors", Choe, et al.
J.of Pharmacokinetics and BioPharmaceutics, vol. 23, No. 4, 1995, pp. 397-406, "In Vivo Pharmacokinetic Study for the Assessment of Poly(L-Aspartic Acid) as a Drug Carrier for Colon-Specific Drug Delivery", Leopold, et al.
Advanced Drug Delivery Reviews, vol. 20, (1996), 195-201, "Limethason as a lipid microsphere preparation: An Overview", Yokoyama, et al.
Journal of Peptide Science, vol. 3 (1997), 141-144, "Evaluation of Carbodiimides Using a Competition Method", Izdebski, et al.
Bioorganic & Medicinal Chemistry Letters, 2005, vol. 15, 3338-3343, "The identification, synthesis, protein crystal structure and in vitro biochemical evaluation of a new 3,4-diarylpyrazole class of Hsp90 inhibitors", Cheung, et al.
Molecular Cancer Therapeutics 2006, vol. 5, 1628-1637, "Preclinical pharmacokinetics and metabolism of a novel diaryl pyrazole resorcinol series of heat shock protein 90 inhibitors", Smith, et al.
Registry Entry for Registry No. 171009-07-07, which entered STN on Dec. 6, 1995, 3 pages.
Registry Entry for Registry No .7689-03-4, which entered STN on Nov. 16, 1984, 3 pages.
Merriam Webster Online Dictionary entry for "Derivative", (http://www.merriam-webster.com/dictionary/derivative), last accessed Feb. 9, 2011, 3 pages.
Office Action dated Oct. 12, 2011 in co-pending U.S. Appl. No. 12/312,157.
Chinese Communication, with English translation, dated Sep. 23, 2011 in co-pending Chinese patent application No. 2007800177809.
International Search Report, dated Jul. 21, 2009 in co-pending PCT application No. PCT/JP2009/058325.
Final Rejection dated Nov. 8, 2011 in co-pending U.S. Appl. No. 12/225,230.
Office Action dated Oct. 25, 2011 in co-pending U.S. Appl. No. 12/312,009.
Colloids and Surfaces B: Biointerfaces V 16 (1999) pp. 217-226, "Micelle-like structures of poly(ethyleneoxide)-block-poly(2-hydroxyethyl aspartamide)-methotrexate conjugates", Li, et al.
Pharmaceutical Research, V. 17, No. 5 (2000) pp. 607-611, "Methotrexate Esters of Poly(EthyleneOxide)-Block-Poly (2-Hydroxyethyl-L-Aspartamide). Part I: Effects of the Level of Methotrexate Conjugation on the Stability of Micelles and on Drug Release", Li, et al.
International Search Report dated Dec. 24, 2003 in international patent application No. PCT/JP03/13838 (now USP 7,495,099).
Taiwanese Communication dated Nov. 30, 2006 in international patent application No. TW092130275 (now USP 7,495,099).
Russian Communication dated Apr. 20, 2007 in international patent application No. RU2005116309 (now USP 7,495,099).
European Communication dated Sep. 25, 2008 in international patent application No. EP03769949.3 (now USP 7,495,099).
International Search Report dated May 11, 2004 in co-pending international patent application No. PCT/JP2004/003647.
Chinese Communicaton dated Oct. 20, 2006 in co-pending international patent application No. CN200480007329.5.
Russian Communication dated Jun. 27, 2007 in co-pending international patent application No. RU2005132309/04.

European Communication dated Feb. 17, 2009 in co-pending international patent application No. EP04721673.4.
Chinese Communication, with English translation, dated Apr. 17, 2009 in co-pending international patent application No. CN200480007329.5.
European Communication dated Jun. 5, 2009 in co-pending international patent application No. EP04721673.4.
Korean Communication dated Nov. 8, 2010 in co-pending international patent application No. 10-2005-7017245.
International Search Report dated Nov. 15, 2005 in co-pending international patent application No. PCT/JP2005/017127.
Taiwanese Communication dated Jul. 22, 2011 in co-pending Taiwanese patent application No. 094132581.
International Search Report dated Jul. 25, 2006 in international patent application No. PCT/JP2006/308826 (now USP 7,700,709).
International Search Report dated May 15, 2007 in co-pending international patent application No. PCT/JP2007/055809.
International Search Report dated Aug. 21, 2007 in co-pending international patent application No. PCT/JP2007/060026.
European Communication dated Oct. 23, 2009 in co-pending international patent application No. EP07743461.1.
Chinese Communication, with English translation, dated Aug. 11, 2010 in co-pending international patent application No. CN2007800177809.
Russian Communication, with English translation, dated May 16, 2011 in co-pending international patent application No. RU2008149932/04.
International Search Report dated Oct. 16, 2007 in co-pending international patent application No. PCT/JP2007/063990.
Chinese Communication dated Nov. 10, 2010 in co-pending international patent application No. CN200780027210.8.
International Search Report dated Jan. 8, 2008 in co-pending international patent applicaton No. PCT/JP2007/068841.
European Communication, dated Oct. 28, 2011 in co-pending European Patent Application No. EP 05783310.5.
Taiwanese Communication, with English translation, dated Dec. 14, 2011 in co-pending Taiwanese Application No. 094132581.
Australian Communication, dated Oct. 28, 2011 in co-pending Australian Patent Application No. 2007252678.
Chinese Communication, with English translation, dated Oct. 10, 2011 in co-pending Chinese Patent Application No. 200880109404.7.
International Search Report mailed Jun. 23, 2009 in co-pending PCT application No. PCT/JP2009/055115.
Chinese Communication, with English translation, dated Aug. 31, 2011 in co-pending Chinese patent application No. 200980110087.5.
International Search Report dated Aug. 10, 2010 in corresponding PCT application No. PCT/JP2010/058034.
Office Action mailed Dec. 15, 2011 in co-pending U.S. Appl. No. 11/662,834.
Final Rejection mailed Feb. 16, 2012 in co-pending U.S. Appl. No. 12/226,962.
Office Action mailed Feb. 21, 2012 in co-pending U.S. Appl. No. 12/312,009.
Notice of Allowance mailed Mar. 1, 2012 in co-pending U.S. Appl. No. 12/312,157.
Journal of Controlled Release, 2001, V. 74, No. 1-3, pp. 295-302, paragraph of "2. Structure of NK911", "Development of the polymer micelle carrier system for doxorubicin", Nakanishi, et al.
Final Rejection mailed Mar. 5, 2013 in co-pending U.S. Appl. No. 12/922,747.
European Communication mailed Jan. 27, 2012 in co-pending European Patent Application No. 07831039.8.
Antimicrobial Agents and Chemotherapy, vol. 2, No. 5, Nov. 1972, pp. 395-401, XP 55016709, ISSN: 0066-4804, "Antiviral Action of Camptothecin", Horwitz, et al.
Final Rejection mailed Mar. 28, 2013 in co-pending U.S. Appl. No. 12/991,041.
Chinese Communication, with English translation, mailed Feb. 22, 2013 in corresponding Chinese Patent Application No. 201080021960.6.
Office Action mailed Apr. 18, 2013 in co-pending U.S. Appl. No. 12/311,086.
Office Action mailed Apr. 6, 2012 in co-pending U.S. Appl. No. 12/225,230.
Miscellaneous Communication mailed Mar. 19, 2012 in co-pending U.S. Appl. No. 12/312,157.
Office Action mailed Apr. 25, 2012 in co-pending U.S. Appl. No. 12/678,620.
Office Action—Restriction—mailed Apr. 27, 2012 in co-pending U.S. Appl. No. 12/922,747.
Final Rejection mailed Aug. 21, 2012 in co-pending U.S. Appl. No. 11/662,834.
Notice of Allowance mailed Aug. 28, 2012 in co-pending U.S. Appl. No. 12/225,230.
Notice of Allowance mailed Aug. 7, 2012 in co-pending U.S. Appl. No. 12/312,009.
Office Action mailed Jul. 30, 2012 in co-pending U.S. Appl. No. 12/922,747.
Office Action—Restriction—mailed Jul. 11, 2012 in co-pending U.S. Appl. No. 12/991,041.
Office Action mailed Aug. 22, 2012 in co-pending U.S. Appl. No. 12/991,041.
Japanese communication, with English translation, mailed Sep. 24, 2013 in co-pending Japanese patent application No. JP2010-503871.
Office Action mailed Oct. 17, 2013 in co-pending U.S. Appl. No. 10/548,998.
Japanese Communication, with English translation, mailed Mar. 26, 2013 in co-pending Japanese Patent Application No. 2008-537500.
Canadian Communication issued Jun. 26, 2013 in co-pending Canadian patent application No. CA 2,664,852.
International Preliminary Report on Patentability, with English translation, issued Apr. 7, 2009 and Apr. 22, 2009 in co-pending PCT application No. PCT/JP2007/068841.
Final Rejection mailed Aug. 28, 2013 in co-pending U.S. Appl. No. 12/311,086.
Office Action mailed Sep. 6, 2013 in co-pending U.S. Appl. No. 12/922,747.
The Merck Index, Fourteenth Edition, 2006, p. 1-6, O'Neil, et al.
Advanced Drug Delivery Reviews, vol. 55, No. 2, Feb. 2003, pp. 217-250, "Effective drug delivery by PEGylated drug conjugates", Greenwald, et al.
European Communication mailed May 24, 2013 in co-pending European patent application No. 09722008.1.
International Search Report and Written Opinion mailed Jan. 24, 2012 in co-pending PCT application No. PCT/JP2011/076373.
Japanese Communication, with partial English translation, mailed May 14, 2013 in co-pending Japanese patent application No. JP 2009-534401.
Chinese Communication, with English translation, mailed Dec. 31, 2013 in co-pending Chinese patent application No. CN 200980110087.5.
Notice of Allowance mailed Jan. 16, 2014 in co-pending U.S. Appl. No. 12/678,620.
International Search Report mailed Dec. 4, 2012 in co-pending PCT application No. PCT/JP2012/072160.
Written Opinion mailed Dec. 4, 2012 in co-pending PCT application No. PCT/JP2012/072160.
International Preliminary Report on Patentability mailed Mar. 20, 2014 in co-pending PCT application No. PCT/JP2012/072160.
Final Rejection mailed Apr. 7, 2014 in co-pending U.S. Appl. No. 12/922,747.

* cited by examiner

*Primary Examiner* — Anand Desai
*Assistant Examiner* — Melissa Mercier
(74) *Attorney, Agent, or Firm* — Nields, Lemack & Frame, LLC

(57) ABSTRACT

A polymer conjugate of a physiologically active substance, which enables drug release independent of a biological enzyme and can be expected to have a high therapeutic effect, is demanded.

Provided is a polymer conjugate of a physiologically active substance, comprising a block copolymer of a polyethylene glycol moiety and a polymer having two or more carboxy groups, in which a substituent represented by general formula (I) or general formula (II) is linked to at least one of the side-chain carboxy groups of the block copolymer via an amide bond [in the formula, $R^8$ and $R^9$ each independently are hydrogen atom or (C1-C6)alkyl which may have a substituent, $R^{10}$ is hydrogen atom, (C1-C40)alkyl which may have a substituent, (C1-C40) aralkyl group which may have a substituent, an aromatic group which may have a substituent, an amino acid residue having a protected carboxy group, or a sugar residue which may have a substituent, CX—CY represents CH—CH or C=C (double bond), and A represents a residue obtained by removing, from a physiologically active substance having one or more hydroxy groups, one of the one or more hydroxy groups].

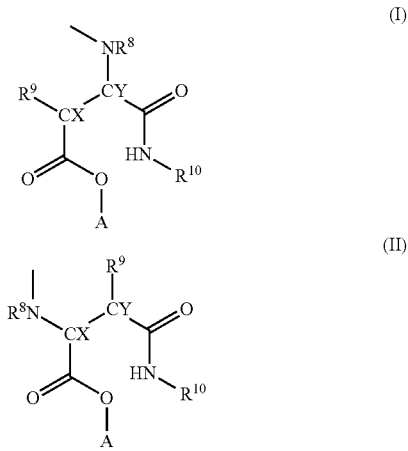

22 Claims, 2 Drawing Sheets

POLYMER CONJUGATE OF BIOACTIVE SUBSTANCE HAVING HYDROXY GROUP

TECHNICAL FIELD

The present invention relates to a polymer conjugate of a physiologically active substance, in which the physiologically active substance having a hydroxy group is linked, through a specific linker, to a side chain of a block copolymer having a polyethylene glycol structural moiety and a polymer with two or more carboxy groups. The present invention also relates to use of the polymer conjugate.

BACKGROUND ART

Polymer conjugates obtained by linking a physiologically active substance such as an anticancer agent or an anti-inflammatory agent, especially a physiologically active substance with low solubility in water, to a polymer carrier have been studied extensively as they are expected to be useful for improving the in vivo pharmacokinetics of the physiologically active substances themselves and the water solubility thereof and the like, and also for increasing the efficacy of the substances as drugs. Particularly, block copolymers in which a hydrophilic polymer and a hydrophobic polymer are bonded to each other may form a micelle having the hydrophobic polymer carrying a physiologically active substance as the inner shell and the hydrophilic polymer covering the surface of the inner shell. The block copolymer are characterized by being capable of maintaining the water solubility as the whole polymer even if the amount of a drug carried thereon is increased.

Patent Literature 1 discloses a compound in which a drug is bonded to a block copolymer of polyethylene glycol and polyaspartic acid without being mediated by a linker, wherein the drug shows water solubility by forming a micelle. Patent Literature 2 discloses a polymer derivative of camptothecins in which a side chain carboxy group of a block copolymer of polyethylene glycol and polyglutamic acid is ester bonded to a phenolic hydroxy group of the camptothecins.

Patent Literature 3 discloses a compound in which a side chain carboxy group of a block copolymer of polyethylene glycol and polyaspartic acid is bonded to an alcoholic hydroxy group of a taxane, and it is also described that a succinic acid monoamide structural moiety which constitutes the polyaspartic acid chain forms an imide bond and simultaneously the ester bond is cleaved to release the taxane. Patent Literature 4 discloses a compound linked with podophyllotoxin. Further, Patent Literature 5 also discloses a compound linked with combretastatins.

CITATION LIST

Patent Literature

Patent Literature 1: Japanese Patent No. 2694923
Patent Literature 2: International Publication No. 2004/039869
Patent Literature 3: International Publication No. 2007/111211
Patent Literature 4: International Publication No. 2007/135910
Patent Literature 5: International Publication No. 2008/010463
Patent Literature 6: International Publication No. 2006/120914

DISCLOSURE OF THE INVENTION

Problems to be Solved by the Invention

Patent Literature 1 discloses doxorubicin as a physiologically active substance, and in the polymer conjugate a block copolymer and doxorubicin are directly bonded to each other through an amide bond. However, in general the amide bond is a chemically stable bonding mode, and therefore the efficacy of such a polymer conjugate is questionable since the in vivo release of doxorubicin by the hydrolysis is very slow.

The polymer conjugate of camptothecins disclosed in Patent Literature 2 is characterized in that a phenolic hydroxy group exhibiting a high reactivity is linked to a carboxylic acid group of polyglutamic acid to form an ester bond enabling easy dissociation of a physiologically active substance. The polymer conjugate of a cytidine metabolic antagonist disclosed in Patent Literature 6 is characterized in that an aromatic amino group exhibiting a high reactivity is linked to a carboxylic acid group of polyglutamic acid to form a bond enabling easy dissociation of a physiologically active substance. As such, releasing a sufficient amount of the physiologically active substance from a polymer conjugate in which a physiologically active substance having an alcoholic hydroxy group or the like with low reactivity is directly bound to polyglutamic acid cannot be easily achieved.

According to the polymer conjugate of Patent Literatures 3, 4, and 5, even from a polymer conjugate of physiologically active substance which has an alcoholic hydroxy group or a phenolic group with low reactivity, a sufficient amount of the physiologically active substance can be released by having a succinic acid monoamide structure moiety in the main chain.

However, from the viewpoint of physical characteristics of a polymer conjugate, broadening the spectrum of various pharmaceutical preparations to choose, improving pharmaceutical efficacy or reducing side effects due to differences in metabolism or distribution, a polymer conjugate useful as a new pharmaceutical agent is demanded.

Means for Solving the Problems

As a result of intensive studies to solve the aforementioned problems, the inventors of the invention have found that a compound in which a physiologically active substance having a hydroxy group is ester-bonded through a specific linker having succinic acid monoamide structure to a side chain of a block copolymer having a polyethylene glycol structural moiety and a polymer having two or more carboxy groups, in particular a side chain of a block copolymer of polyethylene glycol-polyglutamic acid, can exhibit a higher therapeutic effect than a compound in which a physiologically active substance is directly bonded to a side chain of a block copolymer of polyethylene glycol-polyglutamic acid. The inventors also found that the release rate suitable for the bound physiologically active substance can be controlled by appropriately selecting an amine component, i.e., a constitutional element of the liker, and therefore completed the invention.

Specifically, the invention relates to the following items (1) to (25).

(1) A polymer conjugate of a physiologically active substance, comprising a block copolymer of a polyethylene glycol moiety and a polymer having two or more carboxy groups, in which a substituent represented by general formula (I) or general formula (II) is linked to at least one of the side-chain carboxy groups of the block copolymer via an amide bond,

[Chemical Formula 1]

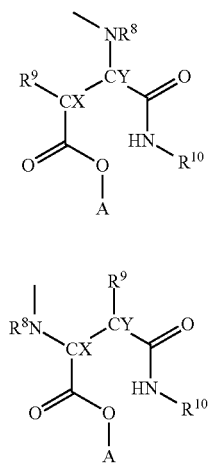

wherein
$R^8$ and $R^9$ each independently represent a hydrogen atom or (C1-C6)alkyl group which may optionally have a substituent,
$R^{10}$ represents hydrogen atom, (C1-C40)alkyl group which may optionally have a substituent, (C1-C40)aralkyl group which may optionally have a substituent, an aromatic group which may optionally have a substituent, an amino acid residue having a protected carboxy group, or a sugar residue which may optionally have a substituent,
CX—CY represents CH—CH or C=C (double bond), and
A represents a residue obtained by removing, from a physiologically active substance having one or more hydroxy groups, one of the one or more hydroxy groups.

(2) The polymer conjugate of a physiologically active substance described in the above (1), in which the polymer having two or more carboxy groups is a polyamino acid or derivative thereof.

(3) The polymer conjugate of a physiologically active substance described in the above (2), in which the polyamino acid is a polyglutamic acid.

(4) The polymer conjugate of a physiologically active substance described in any one of the above (1) to (3) being a compound represented by general formula (III)

[Chemical Formula 2]

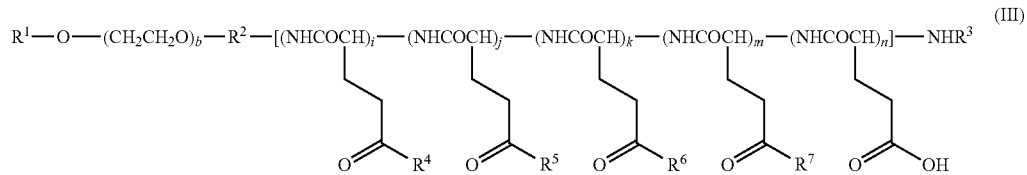

$R^1$ represents hydrogen atom or (C1-C6)alkyl group,
$R^2$ represents a linking group,
$R^3$ represents hydrogen atom or (C1-C6)acyl group, $R^4$ represents a substituent represented by general formula (I) or general formula (II)

[Chemical Formula 3]

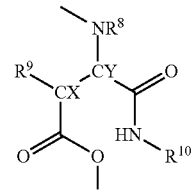

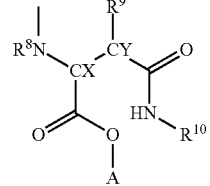

in which $R^8$, $R^9$, $R^{10}$, CX—CY, and A have the same meanings as above,
$R^5$ represents a substituent represented by general formula (IV) or general formula (V)

[Chemical Formula 4]

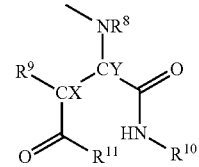

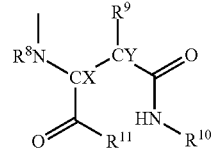

in which $R^8$, $R^9$, $R^{10}$, and CX—CY have the same meanings as above,
$R^{11}$ represents one or more substituents selected from a group consisting of hydroxy group, an aromatic amino group which may optionally have a substituent, (C1-C30)alkoxy group which may optionally have a substituent, (C1-C30)aralkyloxy group which may optionally have a substituent, (C1-C30)alkylamino group which may optionally have a substituent, di(C1-C30) alkylamino group which may optionally have a substituent, an amino acid having a protected carboxy group, and $NR^{12}CONHR^{13}$, wherein $R^{12}$ and $R^{13}$, which may be the same or different from each other, represent (C3-C6)cyclic alkyl group, or (C1-C5)alkyl group which may optionally be substituted with a tertiary amino group, $R^6$ represents a substituent represented by general formula (VI)

[Chemical Formula 5]

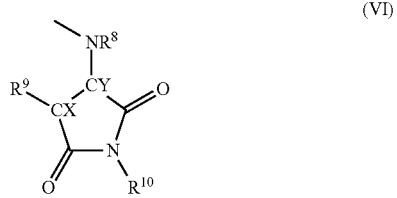

(VI)

in which $R^8$, $R^9$, $R^{10}$, and CX—CY have the same meanings as above, $R^7$ represents a substituent selected from a group consisting of (C1-C30)alkoxy group, (C1-C30)aralkyloxy group, (C1-C30)alkylamino group, di(C1-C30)alkylamino group, an amino acid having a protected carboxy group, and $NR^{12}CONHR^{13}$, wherein $R^{12}$ and $R^{13}$, which may be the same or different from each other, represent (C3-C6)cyclic alkyl group, or (C1-C5)alkyl group which may optionally be substituted with a tertiary amino group, b is an integer from 5 to 11,500, i is an integer from 1 to 200, j, k, m, and n each represent an integer from 0 to 200 with the proviso that i+j+k+m+n represents an integer from 2 to 200.

(5) The polymer conjugate of a physiologically active substance described in the above (4), in which $R^1$ is (C1-C3)alkyl group, $R^2$ is (C2-C6)alkylene group, $R^3$ is (C1-C3)acyl group, b is an integer from 100 to 300, i is an integer from 1 to 90, and j, k, m, and n each represent an integer from 0 to 90 with the proviso that i+j+k+m+n is an integer from 6 to 90.

(6) The polymer conjugate of a physiologically active substance described in the above (4) or (5), in which $R^1$ is methyl group, $R^2$ is trimethylene group, $R^3$ is acetyl group, $R^8$ and $R^9$ in $R^4$, $R^5$ and $R^6$ are all hydrogen atoms, and CX—CY is CH—CH.

(7) The polymer conjugate of a physiologically active substance described in any one of (1) to (6) above, in which the physiologically active substance having one or more hydroxy groups is an anticancer agent.

(8) The polymer conjugate of a physiologically active substance described in (7) above, in which the anticancer agent is a taxoids.

(9) The polymer conjugate of a physiologically active substance described in (8) above, in which the taxoids are paclitaxel or docetaxel.

(10) The polymer conjugate of a physiologically active substance described in (7) above, in which the anticancer agent is podophyllotoxins.

(11) The polymer conjugate of a physiologically active substance described in (10) above, in which the podophyllotoxins are podophyllotoxin, etoposide, or teniposide.

(12) The polymer conjugate of a physiologically active substance described in (7) above, in which the anticancer agent is combretastatins.

(13) The polymer conjugate of a physiologically active substance described in (12) above, in which the combretastatins are combretastatin A1 or combretastatin A4.

(14) The polymer conjugate of a physiologically active substance described in (7) above, in which the anticancer agent is a nucleic acid-based anticancer agent.

(15) The polymer conjugate of a physiologically active substance described in (14) above, in which the nucleic acid-based anticancer agent is gemcitabine, capecitabine, doxifluridine, cytarabine, or 3'-ethynylcytidine.

(16) The polymer conjugate of a physiologically active substance described in (7) above, in which the anticancer agent is camptothecin or derivative thereof.

(17) The polymer conjugate of a physiologically active substance described in (7) above, in which the anticancer agent is doxorubicin, amrubicin, or aclacinomycin.

(18) The polymer conjugate of a physiologically active substance described in any one of (1) to (6) above, in which the physiologically active substance having one or more hydroxy groups is an anti-inflammatory agent.

(19) The polymer conjugate of a physiologically active substance described in (18) above, in which the anti-inflammatory agent is a steroid anti-inflammatory agent.

(20) The polymer conjugate of a physiologically active substance described in any one of (1) to (6) above, in which the physiologically active substance having one or more hydroxy groups is a pain relieving agent, a hair growing agent, or a myocardial protective agent having an effect of decreasing myocardial infarction size.

(21) The polymer conjugate of a physiologically active substance described in (20) above, in which the pain relieving agent, hair growing agent, or myocardial protective agent having an effect of decreasing myocardial infarction size is adenosine.

(22) The polymer conjugate of a physiologically active substance described in any one of (1) to (21) above, characterized in that the polymer conjugate forms a micelle in water.

(23) A pharmaceutical agent containing the polymer conjugate of a physiologically active substance described in any one of (1) to (22) above as an effective component.

(24) An anticancer agent containing the polymer conjugate of a physiologically active substance described in any one of (7) to (17) above as an active ingredient.

(25) An anti-inflammatory agent containing the polymer conjugate of a physiologically active substance described in (18) or (19) above as an active ingredient.

Effects of the Invention

The polymer conjugate of a physiologically active substance according to the invention is a compound in which the physiologically active substance having a hydroxy group is bonded to a side chain of a block copolymer of polyethylene glycol and polyglutamic acid through a specific linker, and it can exhibit a high biological effect. As being capable of releasing the physiologically active substance under physiological conditions without depending on hydrolyzing enzymes in the body, the polymer conjugate of the invention is expected to achieve efficacious therapeutic effects of the physiologically active substance without being affected by differences among individuals. Furthermore, the release rate of the bound physiologically active substance can be controlled suitably by selecting appropriately an amine component as a constitutional element of the linker.

BEST MODE FOR CARRYING OUT THE INVENTION

Figure 1:
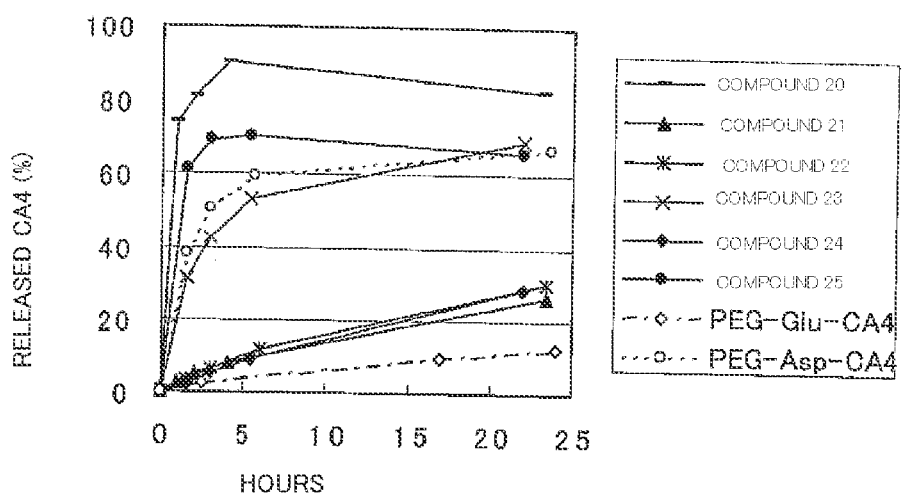
FIG. 1 illustrates the ratio of the amount of combretastatin A4 (CA4) released from Compound 20 to Compound of the present Examples and the comparative compound (PEG-Glu-CA4 and PEG-Asp-CA4), based on the total amounts of bound combretastatin in PBS solution (phosphate buffered physiological saline, pH 7.1) at 37° C.

The polymer conjugate of a physiologically active substance, comprising a block copolymer of a polyethylene glycol structural moiety and a polymer having two or more carboxy groups, in which a substituent represented by general formula (I) or general formula (II) is linked to at least one of the side-chain carboxy groups of the block copolymer via an amide bond. In the formula, $R^8$ and $R^9$ each independently represent a hydrogen atom or (C1-C6)alkyl group which may optionally have a substituent, $R^{10}$ represents hydrogen atom, (C1-C40)alkyl group which may optionally have a substituent, (C1-C40)aralkyl group which may optionally have a substituent, an aromatic group which may optionally have a substituent, an amino acid residue having a protected carboxy group, or a sugar residue which may optionally have a substituent, CX—CY represents CH—CH or C=C (double bond), and A represents a residue obtained by removing, from a physiologically active substance having one or more hydroxy groups, one of the one or more hydroxy groups.

In the polymer conjugate of a physiologically active substance of the invention, the polymer having two or more carboxy groups in the block copolymer having a polyethylene glycol structural moiety and a polymer having two or more carboxy groups may include a polymer obtained by polymerization of low molecular weight monomer having carboxy group on side chain and a polymer obtained by introducing carboxy group by using halogeno acetic acid, for example, to a polymer of low molecular weight monomer having a functional group other than carboxy group (e.g., hydroxy group).

Examples of the polymer may include polyglutamic acid, polyaspartic acid, polyserine, polycysteine, polytyrosine, polylysine, polymalic acid, dextran, and partially oxidized product thereof, and polyuronic acid. The polymer may preferably include polyacidic amino acids such as polyglutamic acid and polyaspartic acid.

As for the polymer having a polyethylene glycol structural moiety and two or more carboxy groups, a block copolymer of polyethylene glycol structural moiety and polyglutamic acid is particularly preferable.

In the linker represented by general formula (I) or general formula (II) for the polymer conjugate of a physiologically active substance of the invention, $R^8$ and $R^9$ each can be hydrogen atom or (C1-C6)alkyl group which may have a substituent, and the examples of the substituent may include methyl, ethyl, and isopropyl groups. Both $R^8$ and $R^9$ may preferably be hydrogen atom.

$R^{10}$ may be a hydrogen atom, (C1-C40)alkyl group which may have a substituent, (C1-C40)aralkyl group which may have a substituent, an aromatic group which may have a substituent, an amino acid residue having a protected carboxy group, or a sugar residue which may have a substituent.

Examples of (C1-C40)alkyl group may include methyl, ethyl, n-propyl, isopropyl, n-butyl, s-butyl, isobutyl, n-pentyl, n-hexyl, and n-stearyl groups. Examples of the substituent group may include phenyl, naphthyl, phenylmethyl, methoxy, ethoxy, and dimethylamino groups.

Examples of (C1-C40)aralkyl group may include benzyl, naphthylmethyl, phenethyl, and 4-phenylbutyl groups. Examples of the substituent group may include methyl group, ethyl group, nitro group, chlorine atom, bromine atom, and dimethylamino group.

Examples of the aromatic group may include groups derived from aniline, nitroaniline, chloroaniline, aminofluorobenzonitrile, aminonaphthalene, aminoflavone, and aminofluorene, etc.

The substitution positions of the substituent are not particularly limited as far as it can be substituted thereon. The number of substituent is not specifically limited, either.

As for the amino acid of the amino acid residue having a protected carboxy group, an amino acid having a protected carboxy group that is commonly used for peptide synthesis can be mentioned. A compound in which the carboxy group of the amino acid is protected by ester or amide is preferable, and examples thereof may include (C1-C12)alkyl ester of alanine, α or β (C1-C12)alkyl ester of aspartic acid, α or γ (C1-C12)alkyl ester of glutamic acid, (C1-C12)alkyl ester of phenylalanine, (C1-C12)alkyl ester of cysteine, (C1-C12) alkyl ester of glycine, (C1-C12)alkyl ester of leucine, (C1-C12)alkyl ester of isoleucine, (C1-C12)alkyl ester of histidine, (C1-C12)alkyl ester of proline, (C1-C12)alkyl ester of serine, (C1-C12)alkyl ester of threonine, (C1-C12)alkyl ester of valine, (C1-C12)alkyl ester of tryptophan, and (C1-C12) alkyl ester of tyrosine. In particular, phenylalanine methyl ester, glycine methyl ester, glycine (4-phenyl-1-butanol) ester, leucine methyl ester, phenylalanine benzyl ester, and phenylalanine (4-phenyl-1-butanol) ester may be preferable. The amino acid may be D form or L form, or mixture thereof.

Examples of the sugar in the sugar residue may include glucosamine, galactosamine, and mannosamine, and examples of the substituent may include acetyl, pivaloyl, benzyl, and methyl groups. The sugar may be D form or L form, or mixture thereof. The number of substituent and the substitution position of the substituent are not particularly limited as long as they are admissible.

With respect to CX—CY in general formula (I) or general formula (II) as a linker in the polymer conjugate of a physiologically active substance of the invention, a linker moiety is required to form a cyclic imide intermediate, and it is CH—CH or C=C (double bond). Examples thereof may include succinic acid monoamide deriviatives and maleic acid monoamide derivatives.

The physiologically active substance of a residue of the physiologically active substance having a hydroxy group that is bound through an ester bond to the linker in the polymer conjugate of a physiologically active substance of the invention may be, but not limited to, a physiologically active substance having a phenolic hydroxy group, primary hydroxy group, or secondary hydroxy group. The residue of the physiologically active substance refers to a moiety of the physiologically active substance compound having one of more hydroxy groups from which the hydroxy group bonded to the linker is eliminated. The substitution positions of phenolic hydroxy group, primary hydroxy group, and secondary hydroxy group may be, but not limited to, the same or different from one another in a single molecule. It may be the same or different from one another among the different molecules. When the physiologically active substance has plural hydroxy groups, the hydroxy groups may bind to the same or different block copolymers, and such embodiment also falls within the scope of the invention.

Examples of the physiologically active substance may include, as an anticancer agent, taxoids such as paclitaxel and docetaxel, podophyllotoxins such as podophyllotoxin, etoposide and teniposide, combretastatins such as combretastatin A1 and combretastatin A4, nucleic acids such as gemcitabine, capecitabine, doxifluridine, cytarabine and 3'-ethynylcytidine, anthracycline glycosides such as doxorubicin, amrubicin and aclacinomycin, and camptothecin and their derivatives; as an anti-inflammatory agent, steroids having phenolic hydroxy group or alcoholic hydroxy group, for example, prednisolone, methylprednisolone, dexamethasone, betamethasone, clobetasol, diflorasone, diflucortolone, flurocinolone acetonide, hydrocortisone, difluprednate, beclomethasone, triamcinolone and alclomethasone; and as a pain relieving agent, a hair growing agent, and a myocardial protective agent having an effect of decreasing myocardial infarction size, adenosine.

Structural formulae of docetaxel, etoposide, combretastatin A4, gemcitabine, prednisolone, paclitaxel, adenosine, capecitabine, and 3'-ethynyl cytidine are given below.

Docetaxel

[Chemical Formula 6]

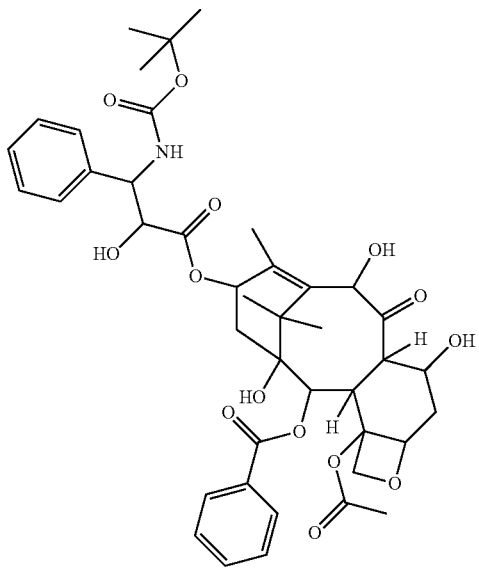

Etoposide

[Chemical Formula 7]

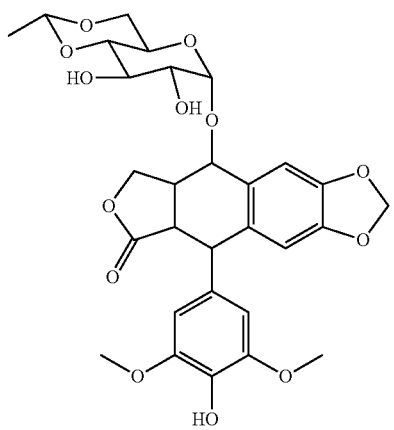

Combretastatin A4

[Chemical Formula 8]

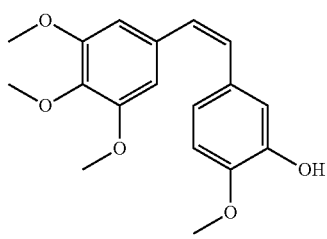

Gemcitabine

[Chemical Formula 9]

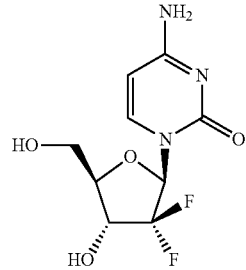

Prednisolone

[Chemical Formula 10]

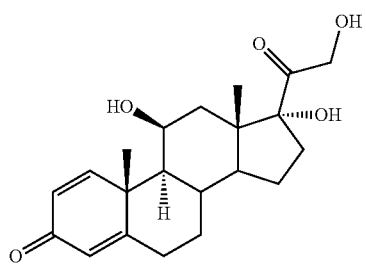

Paclitaxel

[Chemical Formula 11]

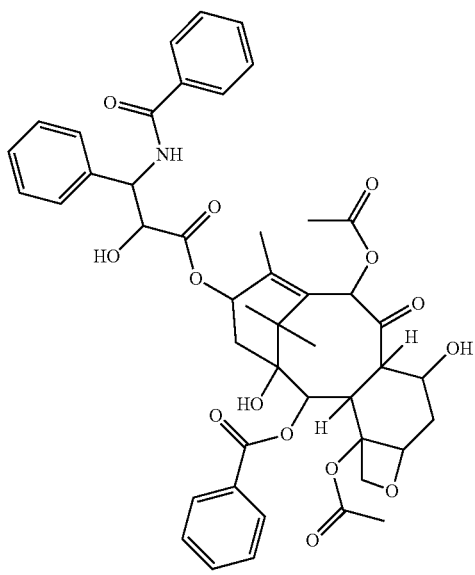

Adenosine

[Chemical Formula 12]

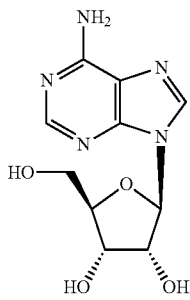

Capecitabine

[Chemical Formula 13]

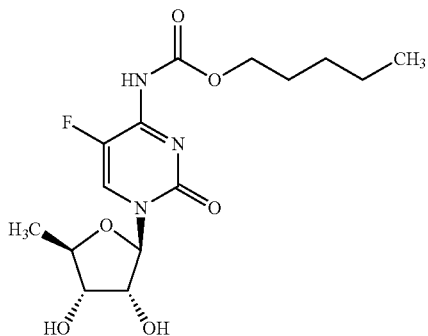

3'-ethynycytidine

[Chemical Formula 14]

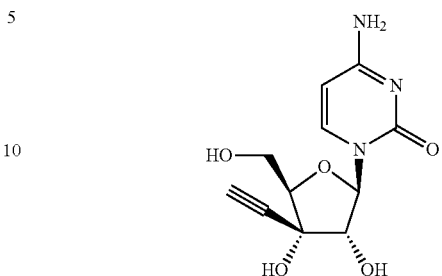

The polymer conjugate of a physiologically active substance may preferably be a compound represented by the general formula (III) [wherein, $R^1$ represents a hydrogen atom or (C1-C6)alkyl group, $R^2$ represents a bonding group, $R^3$ represents a hydrogen atom or (C1-C6)acyl group, $R^4$ represents a substituent represented by the general formula (I) or the general formula (II) [wherein, $R^8$, $R^9$, $R^{10}$, CX—CY, and A have the same meanings as above], $R^5$ represents a substituent represented by general formula (IV) or general formula (V) [wherein, $R^8$, $R^9$, $R^{10}$, and CX—CY have the same meanings as above, $R^{11}$ represents one or more substituents selected from a group consisting of a hydroxy group, an aromatic amino group which may have a substituent, (C1-C30)alkoxy group which may have a substituent, (C1-C30)aralkyloxy group which may have a substituent, (C1-C30)alkylamino group which may have a substituent, di(C1-C30)alkylamino group which may have a substituent, an amino acid having a protected carboxy group, and $NR^{12}CONHR^{13}$, and $R^{12}$ and $R^{13}$, which may be the same or different from each other, represent (C3-C6)cyclic alkyl group, or (C1-C5)alkyl group which may be substituted with a tertiary amino group], $R^6$ represents a substituent represented by general formula (VI) [wherein, $R^8$, $R^9$, $R^{10}$, and CX—CY have the same meanings as above], $R^7$ represents a substituent selected from a group consisting of (C1-C30)alkoxy group, (C1-C30)aralkyloxy group, (C1-C30)alkylamino group, di(C1-C30)alkylamino group, an amino acid having a protected carboxy group and $NR^{12}CONHR^{13}$, $R^{12}$ and $R^{13}$, which may be the same or different from each other, represent (C3-C6)cyclic alkyl group, or (C1-C5)alkyl group which may be substituted with a tertiary amino group, b represents an integer from 5 to 11,500, i represents an integer from 1 to 200, j, k, m, and n each represent an integer from 0 to 200, with the proviso that i+j+k+m+n represents an integer from 2 to 200].

Examples of the (C1-C6)alkyl group for $R^1$ in general formula (III) may include linear or branched (C1-C6)alkyl group, and preferably, (C1-C4)alkyl group, e.g., methyl, ethyl, n-propyl, and n-butyl groups. Of these, methyl group may be particularly preferable.

The bonding group for $R^2$ in general formula (III) may preferably be (C2-C6)alkylene group, such as ethylene group, trimethylene group, and tetramethylene group, more preferably trimethylene group.

The (C1-C6) acyl group for $R^3$ in general formula (III) may be, but not limited to, (C1-C3) ac group, such as formyl, acetyl, and propionyl groups, more preferably acetyl group.

Examples of $R^8$ and $R^9$ in general formula (I) or general formula (II) for $R^4$ in general formula (III) may include the same groups as the $R^8$ and $R^9$ in general formula (I) or general formula (II) described above, and the preferred group is also hydrogen atom.

Examples of $R^{10}$ in general formula (I) or general formula (II) for the $R^4$ in general formula (III) may include the same groups as $R^{10}$ in general formula (I) or general formula (II) described above.

Examples of the residue A as the physiologically active substance in general formula (I) or general formula (II) for $R^4$ in general formula (III) may include the same residue of the physiologically active substance A in the general formula (I) or the general formula (II) described above.

Examples of $R^8$, $R^9$, $R^{10}$, and CX—CY in general formula (IV) or general formula (V) for $R^5$ in general formula (III) may include the same groups as $R^8$, $R^9$, $R^{10}$, and CX—CY in general formula (I) or general formula (II) described above.

Examples of the aromatic amino group which may have a substituent as $R^{11}$ in general formula (IV) or general formula (V) for $R^5$ in general formula (III) may include anilino group, naphthylamino group, pyridylamino group, an amino group of adenosine, an amino group of citidine, and an amino group of a nucleic acid.

Examples of the (C1-C30)alkoxy group in the (C1-C30) alkoxy group which may have a substituent as $R^{11}$ in general formula (IV) or general formula (V) for $R^5$ in general formula (III) may include linear or branched (C1-C10)alkoxy group, more preferably linear or branched (C1-C10)alkoxy group such as methoxy, ethoxy, n-propoxy, i-propoxy, n-butoxy, and t-butoxy groups. Examples of the substituent may include phenyl, naphthyl, phenylmethyl, methoxy, ethoxy, and dimethylamino groups.

Examples of the (C1-C30)aralkyloxy group in the (C1-C30)aralkyloxy group which may have a substituent may include linear or branched (C1-C30)aralkyloxy group, more preferably linear or branched (C1-C12)aralkyloxy group such as benzyloxy group and a 4-phenylbutoxy group. Examples of the substituent may include methyl, ethyl, nitro, chloro, bromo, and dimethylamino groups.

Examples of the (C1-C30)alkylamino group or di(C1-C30) alkylamino group in the (C1-C30)alkylamino group or di(C1-C30)alkylamino group which may have a substituent may include linear or branched (C1-C30)alkylamino group and di(C1-C30)alkylamino group, more preferably linear or branched (C1-C20)alkylamino group and di(C1-C20)alkylamino group such as methylamino, ethylamino, n-propylamino, i-propylamino, n-butylamino, t-butylamino, dimethylamino, diethylamino, and di(n-butyl)amino groups. Examples of the substituent may include phenyl, naphthyl, phenylmethyl, methoxy, ethoxy, and dimethylamino groups.

Examples of the amino acid having a protected carboxy group may include the same amino acids as the amino acid having a protected carboxy group for the $R^{10}$ in general formula (I) or general formula (II) described above, and the preferred amino acids are also the same.

$NR^{12}CONHR^{13}$ [$R^{12}$ and $R^{13}$ can be the same or different from each other, and represents (C3-C6)cyclic alkyl group or (C1-C5)alkyl group which may be substituted with a tertiary amino group] as $R^{11}$ in general formula (IV) or general formula (V) for $R^5$ in general formula (III) may be, but not limited to, cyclohexylamino carbonyl cyclohexylamino group and an isopropylamino carbonyl isopropylamino group.

Examples of the $R^8$, $R^9$, $R^{10}$, and CX—CY in general formula (VI) for $R^6$ in general formula (III) may include the same groups as the $R^8$, $R^9$, $R^{10}$, and CX—CY in general formula (I) or general formula (II) described above, and the preferred groups are also the same.

Examples of the (C1-C30)alkoxy group, (C1-C30)aralkyloxy group, (C1-C30)alkylamino group, and di(C1-C30) alkylamino group for $R^7$ in general formula (III) may include each group described above as $R^{11}$ in general formula (IV) or general formula (V) for $R^5$ in general formula (III), and the preferred groups are also the same. Further, examples of the amino acid having a protected carboxy group may include the amino acids described above as $R^{11}$ in general formula (IV) or general formula (V) for $R^5$ in general formula (III). Examples of $NR^{12}CONHR^{13}$ [$R^{12}$ and $R^{13}$ may be the same or different from each other and represent (C3-C6)cyclic alkyl group or (C1-C5)alkyl group which may be substituted with a tertiary amino group] may include the groups described above as $R^{11}$ in general formula (IV) or general formula (V) for $R^5$ in general formula (III). The preferred groups are also the same.

The total number of total glutamic acids in the polymer conjugate of the physiologically active substance of the invention that is represented by general formula (III), is expressed as i+j+k+m+n, and it is within the range of about 3 to 200, more preferably about 6 to 90, still more preferably 6 to 60, and most preferably 13 to 40.

The ratio of number of glutamic acid linked to physiologically active substance (i.e. "i") compared to the total number of glutamic acids (i+j+k+m+n) is from 1% to 100%, preferably from 3% to 100%, and still more preferably from 4% to 100%. Further, in terms of the number of glutamic acids (i.e. "i"), it is 1 to 200, preferably about 1 to 90, and more preferably about 2 to 60.

The each constituting unit in glutamic acid structure for the polymer conjugate of the physiologically active substance represented by the general formula (III) may be bonded in any order without limitation, and it may be bonded to form a block type or a random type.

The symbol "b" in the general formula (III) is an integer of about 5 to 11,500, preferably an integer of 8 to 2,300, and more preferably an integer of 100 to 300.

The molecular weight of the polyethylene glycol structural moiety in the general formula (II) is about 300 to 500,000, preferably about 500 to 100,000, more preferably about 1,000 to 50,000.

The molecular weight of the polymer conjugate of physiologically active substance according to the invention is about 500 to 600,000, preferably about 600 to 110,000, more preferably about 1,100 to 80,000. According to the invention, the term "molecular weight" refers to a weight average molecular weight determined by the GPC method.

The polymer conjugate of a physiologically active substance according to the invention may form in water a micelle having a polyethylene glycol structural moiety as the outer shell and a hydrophobic polymer to which a physiologically active substance is bonded through a linker as the inner shell.

Production of the polymer conjugate of a physiologically active substance according to the invention is characterized in that the side chain carboxy group of a block copolymer having polyethylene glycol structural moiety and polyglutamic acid is amide-bonded to, as a linker moiety, succinic acid monoamide derivatives having an amino group and a protected carboxy group or maleic acid monoamide derivatives having an amino group and a protected carboxy group by using a dehydrating condensation agent in an organic solvent, and the carboxy group generated by deprotection of the protective group and the hydroxyl group of the physiologically active substance having hydroxyl group are ester-boned by using a dehydrating condensation agent in an organic solvent.

Specifically, methoxy polyethylene glycol-polyglutamic acid block copolymer prepared according to the method disclosed in International publication No. 2006/120914 and an aminosuccinic acid monoamide compound in which the carboxy group is protected with a benzyl group, etc. are dissolved in an organic solvent which can dissolve both compounds, preferably an aprotic polar solvent like N,N-dimethyl formamide (DMF), 1,3-dimethyl-2-imidazolidinone (DMI), and N-methylpyrrolidone (NMP), and condensed to each other by subjecting them to a reaction using a dehydrating condensation agent such as dicyclohexylcarbodiimide (DCC), diisopropylcarbodiimide (DIPC), 1-ethyl-3-(3-dimethylaminopropyl)carbodiimide (WSC) hydrochloride salt, and 1-ethoxycarbonyl-2-ethoxy-1, 2-dihydroxyquinolinone (EEDQ) at 0° C. to 180° C., and preferably 5° C. to 50° C., the protective group of the carboxy group is deprotected, and the physiologically active substance having hydroxy group is bonded thereto by using the same dehydrating condensation agent and in the same solvent as those described above.

For the condensation reaction, a reaction aid agent such as N,N-dimethylaminopyridine (DMAP) and 1-hydroxy-1H-benzotriazole (HOBt) may be used.

$NR^{12}CONHR^{13}$ in $R^7$ or $R^{11}$ may also be obtained according to the reaction which uses the above carbodiimides as a condensation agent.

For producing a compound having (C1-C30)alkoxy group, (C1-C30)aralkyloxy group, (C1-C30)alkylamino group, di(C1-C30)alkylamino group, or an amino acid having a protected carboxy group for $R^7$ in general formula (II) or $R^{11}$ in general formula (IV) or general formula (V) for $R^5$ in general formula (III), the carboxy group of block copolymer may be activated by a method generally used for dehydration condensation followed by reaction in a basic condition with a corresponding alcohol, a corresponding amine, or an amino acid residue having a protected carboxy group in an amount to achieve the desired bonding. Further, corresponding alcohol, a corresponding amine, or an amino acid having a protected carboxy group, etc. are activated by a method generally used for dehydration condensation and the method in which the activated alcohol, amine, and amino acid are reacted with a polymer may also be used.

Thereafter, it is subjected to a dehydration condensation reaction with succinic acid monoamide derivatives having an amino group and a protected carboxy group or succinic acid monoamide derivatives having an amino group and a protected carboxy group, and the carboxy group generated by deprotection of the protective group and the hydroxy group of the physiologically active substance having hydroxy group are ester-boned by using a dehydrating condensation agent.

Alternatively, it is also possible that the side chain carboxy group of a block copolymer having polyethylene glycol structural moiety and a polymer having carboxy group is subjected to a dehydration condensation with succinic acid monoamide derivatives having an amino group and a protected carboxy group or succinic acid monoamide derivatives having an amino group and a protected carboxy group, the remaining carboxy groups are activated, (C1-C30)alkoxy group, (C1-C30)aralkyloxy group, (C1-C30)alkylamino group, di(C1-C30)alkylamino group or an amino acid having a protected carboxy group is introduced to the remaining carboxy groups, and the resultant may be reacted with a physiologically active substance having hydroxy group as described above.

Alternatively, different alcohols, amines and the like may be repeatedly reacted to introduce various substituents to the groups.

Further, when the physiologically active substance having hydroxy group has another functional group which can react with carboxy group, the functional group may be protected and later deprotected at appropriate stage after condensation, if necessary.

The method for manufacturing the polymer conjugate of a physiologically active substance according to the invention is not limited to the aforementioned methods.

The polymer conjugate of a physiologically active substance according to the invention can be used as a pharmaceutical agent which is indicated for a disease for which the physiologically active substance carried on the conjugate have an efficacy. Examples of the pharmaceutical product may include an anticancer agent and an anti-inflammatory agent. The polymer derivatives may be used in a dosage form which is conventionally used, including injections, tablets, and powders. For formulation process, pharmaceutically acceptable carriers which are conventionally used, include, for example, binding agents, lubricating agents, disintegrating agents, solvents, vehicles, solubilizing agents, dispersing agents, stabilizing agents, suspending agents, preservatives, soothing agents, colorants, and flavors.

The polymer conjugate of a physiologically active substance according to the invention is used preferably as an injection, and usually water, a physiological saline, a 5% glucose or mannitol liquid, a water-soluble organic solvent (for example, glycerol, ethanol, dimethyl sulfoxide, N-methylpyrrolidone, polyethylene glycol, cremophor, and a mixture thereof) or a mixture of water and the water-soluble organic solvents may be used.

The dosage of the polymer conjugate of a physiologically active substance according to the invention may vary as a matter of course, depending on the characteristics of physiologically active substance as well as the sex, age, physiological condition, pathological condition and the like of a patient. The conjugate is parenterally administered, typically at a dose of 0.01 to 500 mg/m$^2$, preferably 0.1 to 250 mg/m$^2$, as an active component per day for an adult. The administration by injection may be performed intravenously, intra-arterially, or into an affected site (a tumor site), for example.

EXAMPLES

Hereinafter, the invention will be illustrated more specifically with reference to Examples. However, the scope of the invention is not limited to these Examples. The Gaussian distribution analysis for measuring the size of the particles (i.e. particle diameter) that are constituted by the product of invention in an aqueous solution was conducted by using a ZetaPotential/Particlesizer NICOMP™ 380ZLS (manufactured by Particle Sizing Systems Co.).

Synthetic Example 1

Synthesis of Compound 1 (Glycine (4-phenyl-1-butanol) ester)

1.0 g of glycine hydrochloride salt (manufactured by Wako Pure Chemical Industries, Ltd.) and 6.7 g of 4-phenyl-1-butano (manufactured Tokyo Chemical Industry Co., Ltd.) were suspended in 5 mL of dioxane added with 5 mL of 4 N-hydrochloric acid/dioxane, and stirred at room temperature for 3 days. The undissolved matters were filtered and washed with 5 mL of dioxane. To the solution obtained by combining the filtrate and the washing solution, 100 mL of diethyl ether was added, and stirred at room temperature for 1 hour. The precipitates were filtered and dried under reduced pressure to obtain 1.7 g of the hydrochloride salt of Compound 1.

$^1$H-NMR (400 MI-Hz, DMSO-d$_6$, ppm): 1.63 (m, 4H), 2.61 (m, 2H), 3.80 (s, 2H), 4.18 (m, 2H), 7.1-7.3 (m, 5H), 8.0-8.6 (br, 2H)

Synthetic Example 2

Synthesis of Compound 2 (phenylalanine (4-phenyl-1-butanol) ester)

1.5 g of phenylalanine hydrochloride salt (manufactured by KOKUSAN CHEMICAL Co. Ltd.) and 6.7 g of 4-phenyl-1-butanol (manufactured Tokyo Chemical Industry Co., Ltd.) were suspended in 5 mL of dioxane, added with 5 mL of 4 N-hydrochloric acid/dioxane, and stirred at room temperature for 3 days. Subsequently, 1.6 g of the hydrochloride salt of Compound 2 was obtained in the same manner as Example 1.

$^1$H-NMR (400 MHz, DMSO-d$_6$, ppm): 1.46 (m, 4H), 2.53 (m, 2H), 2.97-3.18 (m, 2H), 4.06 (m, 2H), 4.27 (dd, 1H), 7.2-7.4 (m, 10H), 8.0-8.8 (br, 2H)

Synthetic Example 3

Synthesis of Compound 3 (aspartic acid β-Benzyl ester-glycine methyl ester)

0.97 g of N-(tert-butoxycarbonyl)aspartic acid β-benzyl ester (manufactured by KOKUSAN CHEMICAL Co., Ltd.) and 0.38 g of glycine methyl ester hydrochloride salt (manufactured by KOKUSAN CHEMICAL Co., Ltd.) were dissolved in 19 mL DMF, added with 0.42 mL of triethylamine, 0.51 g of HOBt, and 0.63 g of WSC hydrochloride salt, and then stirred overnight at room temperature. The reaction solution was extracted with ethyl acetate, and washed with cold water, dil. hydrochloric acid, saturated aqueous solution of sodium hydrogen carbonate, and saturated brine in order. Ethyl acetate was distilled off under reduced pressure followed by vacuum drying to obtain 1.2 g of solid. The resulting solid was dissolved in 15 mL of ethyl acetate, added with 15 mL of 4 N—HCl/ethyl acetate, and stirred at room temperature for 1 hour. The reaction solution was added with 120 mL of diethyl ether, stirred at room temperature for 2 hours, and the solvent was removed by decanting. Subsequently, the solid was washed with diethyl ether. The solid matter in oil state was dried under reduced pressure to obtain 0.86 g of the hydrochloride salt of Compound 3.

$^1$H-NMR (400 MHz, DMSO-d$_6$, ppm): 2.94 (m, 4H), 3.63 (s, 3H), 3.92 (ddd, 2H), 4.18 (dd, 1H), 5.15 (m, 2H), 7.3-7.4 (m, 5H), 8.3 (br, 2H), 8.93 (t, 1H)

Synthetic Example 4

Synthesis of Compound 4 (aspartic acid β-benzyl ester-phenylalanine methyl ester)

1.3 g of N-(tert-butoxycarbonyl)aspartic acid β-benzyl ester (manufactured by KOKUSAN CHEMICAL Co., Ltd.) and 0.86 g of phenylalanine methyl ester hydrochloride salt (manufactured by KOKUSAN CHEMICAL Co., Ltd.) were dissolved in 23 mL of DMF, added with 0.56 mL of triethylamine, 0.73 g of HOBt, and 0.84 g of WSC hydrochloride salt, and then stirred overnight at room temperature. Subsequently, 2.0 g of solid was obtained in the same manner as in Example 3. The resulting solid was dissolved in 20 mL of ethyl acetate, added with 20 mL of 4 N—HCl/ethyl acetate, and stirred at room temperature for 1 hour. Subsequently, the solid was dried under reduced pressure in the same manner as in Example 3 to obtain 1.65 of the hydrochloride salt of Compound 4.

$^1$H-NMR (400 MHz, DMSO-d$_6$, ppm): 2.64 (m, 2H), 2.98 (dd, 2H), 3.09 (dd, 28), 3.64 (s, 3H), 4.07 (dd, 1H), 4.60 (m, 1H), 5.12 (m, 2H), 7.1-7.3 (m, 10H), 8.0 (br, 2H), 8.96 (d, 1H)

Synthetic Example 5

Synthesis of Compound 5 (aspartic acid β-benzyl ester-leucine methyl ester)

1.3 g of N-(tert-butoxycarbonyl)aspartic acid β-benzyl ester (manufactured by KOKUSAN CHEMICAL Co., Ltd.) and 0.73 g of leucine methyl ester hydrochloride salt (manufactured by KOKUSAN CHEMICAL Co., Ltd.) were dissolved in 23 mL of DMF, added with 0.56 mL of triethylamine, 0.73 g of HOBt, and 0.84 g of WSC hydrochloride salt, and then stirred overnight at room temperature. Subsequently, 1.9 g of solid was obtained in the same manner as in Example 3. The resulting solid was dissolved in 20 mL of ethyl acetate, added with 20 mL of 4 N—HCl/ethyl acetate, and stirred at room temperature for 1 hour. Subsequently, the solid was dried under reduced pressure in the same manner as in Example 3 to obtain 1.51 g of the hydrochloride salt of Compound 5.

$^1$H-NMR (400 MHz, DMSO-d$_6$, ppm): 0.88 (dd, 6H), 1.5-1.8 (m, 3H), 2.84 (dd, 2H)-1, 2.95 (dd, 2H), 3.62 (s, 3H), 4.15 (dd, 1H), 4.32 (m, 1H), 5.17 (m, 2H), 7.3-7.4 (m, 5H), 8.0 (br, 2H), 8.79 (d, 1H)

Synthetic Example 6

Synthesis of Compound 6 (aspartic acid β-benzyl ester-glycine (4-phenyl-1-butanol) ester)

1.3 g of N-(tert-butoxycarbonyl) aspartic acid β-benzyl ester (manufactured by KOKUSAN CHEMICAL Co., Ltd.) and 0.97 g of the hydrochloride salt of Compound 1 obtained from Synthetic example 1 were dissolved in 23 mL of DMF, added with 0.56 mL of triethylamine, 0.73 g of HOBt, and 0.84 g of WSC hydrochloride salt, and then stirred overnight at room temperature. Subsequently, 2.0 g of solid was obtained in the same manner as in Example 3. The resulting solid was dissolved in 20 mL of ethyl acetate, added with 20 mL of 4 N—HCl/ethyl acetate, and stirred at room temperature for 1 hour. Subsequently, the solid was dried under reduced pressure in the same manner as in Example 3 to obtain 1.72 g of the hydrochloride salt of Compound 6.

$^1$H-NMR (400 MHz, DMSO-d$_6$, ppm): 1.59 (m, 4H), 2.59 (m, 2H), 2.80 (dd, 2H), 2.93 (dd, 2H), 3.91 (ddd, 2H), 4.07 (m, 3H), 5.15 (m, 2H), 7.2-7.4 (m, 10H), 8.8 (br, 1H)

Synthetic Example 7

Synthesis of Compound 7 (aspartic acid β-benzyl ester n-butylamide)

1.3 g of N-(tert-butoxycarbonyl)aspartic acid β-benzyl ester (manufactured by KOKUSAN CHEMICAL Co., Ltd.) and 0.40 g of n-butylamine were dissolved in 23 mL of DMF, added with 0.73 g of HOBt, and 0.84 g of WSC hydrochloride salt, and then stirred overnight at room temperature. Subsequently, 1.54 g of solid was obtained in the same manner as in Example 3. The resulting solid was dissolved in 20 mL of ethyl acetate, added with 20 mL of 4 N—HCl/ethyl acetate, and stirred at room temperature for 1 hour. Subsequently, the solid was dried under reduced pressure in the same manner as in Example 3 to obtain 1.24 g of the hydrochloride salt of Compound 7.

$^1$H-NMR (400 MHz, DMSO-d$_6$, ppm): 0.85 (t, 3H), 1.27 (m, 2H), 1.37 (m, 2H), 2.91 (ddd, 2H), 3.09 (m, 2H), 4.02 (dd, 2H), 5.14 (m, 2H), 7.39 (m, 5H), 8.15 (br, 2H), 8.43 (t, 1H)

Synthetic Example 8

Synthesis of Compound 8 (amide conjugate of a block copolymer consisting of methoxy polyethylene glycol moiety having molecular weight of 12,000 and polyglutamic acid moiety having polymerization number of 21 and aspartic acid β-benzyl ester-glycine methyl ester: in general formula (iii), $R^1$=me (methyl group), $R^2$=trimethylene group, $R^3$=Ac (acetyl group), $R^8$ and $R^9$=hydrogen atom, $R^{10}$=glycine methyl ester residue, $R^{11}$=benzyloxy group, i+j+k+m+n=21, b=273)

2.0 g of methoxy polyethylene glycol-polyglutamic acid block copolymer which has been produced according to the method described in International Publication No. 2006/120914 and Compound 3 (0.86 g) obtained from Synthetic example 3 were dissolved in 40 mL of DMF, added with 0.36 ma of triethylamine, 0.04 g of DMAP, and 0.90 mL of DIPC at 25° C., and then stirred for 20 hours at 25° C. To the reaction solution, 80 ml of ethanol and 320 mL of diisopropyl ether were added and stirred for 2 hours at room temperature. The precipitates were filtered and washed with ethanol/diisopropyl ether (1/4 (v/v), 40 mL). The resulting precipitates were dissolved at 5° C. in 44 mL of acetonitrile and 11 mL of water, passed through an ion exchange column (trade name: DOWEX 50 (H$^+$), manufactured by Dow Chemical Company, 5 mL), and then eluted with acetonitrile/water (5/1 (v/v), 15 mL). To the resulting eluted fraction, 75 mL of water was added and acetonitrile was distilled off under reduced pressure. Subsequently, Compound 8 (2.71 g) was obtained by freeze drying.

2 N-aqueous sodium hydroxide solution was added to Compound 8 and stirred at 40° C. for 1 hour. The released benzyl alcohol was analyzed by HPLC (high performance liquid chromatography), and the content of aspartic acid β-benzyl ester-glycine methyl ester bound to Compound 8 was calculated from the amount of benzyl alcohol obtained from the calibration curve established with commercially available benzyl alcohol. As a result, the content of the bonded aspartic acid β-benzyl ester-glycine methyl ester was 28.3% (w/w), and the ratio of j compared to the total glutamic acid (i+j+k+m+n) was 93%. On the carbonyl group of the side chain of remaining glutamic acid, isopropylamino carbonyl isopropylamide group or hydroxy group was bonded.

Synthetic Example 9

Synthesis of Compound 9 (amide conjugate of a block copolymer consisting of methoxy polyethylene glycol moiety having molecular weight of 12,000 and polyglutamic acid moiety having polymerization number of 21 and aspartic acid β-benzyl ester-phenylalanine methyl ester: in general formula (III), $R^1$=Me, $R^2$=trimethylene group, $R^3$=Ac, $R^8$ and $R^9$=hydrogen atom, $R^{10}$=phenylalanine methyl ester residue, $R^{11}$=benzyloxy group, i+j+k+m+n=21, b=273)

3.09 g of methoxy polyethylene glycol-polyglutamic acid block copolymer which has been produced according to the method described in international Publication No. 2006/120914 and Compound 4 (1.65 g) obtained from Synthetic example 4 were dissolved in 55 mL of DMF, added with 0.55 mL of triethylamine, 0.05 g of DMAP, and 1.37 mL of DIPC at 25° C., and then stirred for 20 hours at 25° C. Subsequently, the precipitates that are obtained in the same manner as Compound 8 were dissolved at 5° C. in 70 mL of acetonitrile and 20 mL of water, passed through an ion exchange column (trade name: DOWEX 50 (H$^+$), manufactured by Dow Chemical Company, 10 mL), and then eluted with acetonitrile/water (5/1 (v/v), 30 mL). To the resulting eluted fraction, 130 mL of water was added and acetonitrile was distilled off under reduced pressure. Subsequently, Compound 9 (4.52 g) was obtained by freeze drying.

The amount of aspartic acid β-benzyl ester-phenylalanine methyl ester bound to Compound 9 was calculated from the amount of benzyl alcohol which has been obtained in the same manner as Compound 8. As a result, the content of the bound aspartic acid β-benzyl ester-phenylalanine methyl ester was 34.0% (w/w), and the ratio of j compared to the total glutamic acid (i+j+k+m+n) was 93%. On the side chain of the remaining glutamic acid, an isopropylamino carbonyl isopropylamide group or a hydroxy group was bonded.

Synthetic Example 10

Synthesis of Compound 10 (amide conjugate of a block copolymer consisting of methoxy polyethylene glycol moiety having molecular weight of 12,000 and polyglutamic acid moiety having polymerization number of 21 and aspartic acid β-benzyl ester-leucine methyl ester: in general formula (III), $R^1$=Me, $R^2$=trimethylene group, $R^3$=Ac, $R^8$ and $R^9$=hydrogen atom, $R^{10}$=leucine methyl ester residue, $R^{11}$=benzyloxy group, i+j+K+m+n=21, b=273)

3.08 g of methoxy polyethylene glycol-polyglutamic acid block copolymer which has been produced according to the method described in International Publication No. 2006/120914 and Compound 5 (1.51 g) obtained from Synthetic example 5 were dissolved in 54 mL of DMF, added with 0.54 mL of triethylamine, 0.05 g of DMAP, and 1.36 mL of DIPC at 25° C., and then stirred for 20 hours at 25° C. Subsequently, the precipitates that are obtained in the same manner as Compound 8 were dissolved at 5° C. in 70 mL of acetonitrile and 20 ml of water, passed through an ion exchange column (trade name: DOWEX 50 (Hi), manufactured by Dow Chemical Company, 10 mL), and then eluted with acetonitrile/water (5/1 (v/v), 30 mL). To the resulting eluted fraction, 130 mL of water was added and acetonitrile was distilled off under reduced pressure. Subsequently, Compound (4.26 g) was obtained by freeze drying.

The content of aspartic acid β-benzyl ester-leucine methyl ester bound to Compound 10 was calculated from the amount of benzyl alcohol which has been obtained in the same manner as Compound 8. As a result, the content of the bound aspartic acid β-benzyl ester-leucine methyl ester was 28.9% (w/w), and the ratio of j compared to the total glutamic acid (i+j+k+m+n) was 81%. On the side chain of the remaining glutamic acid, isopropylamino carbonyl isopropylamide group or hydroxy group was bonded.

Synthetic Example 11

Synthesis of Compound 11 (amide conjugate of a block copolymer consisting of methoxy polyethylene glycol moiety having molecular weight of 12,000 and polyglutamic acid moiety having polymerization number of 21 and aspartic acid β-benzyl ester-glycine (4-phenyl-butanol) ester: in general formula (III), $R^1$=Me, $R^2$=trimethylene group, $R^3$=Ac, $R^8$ and $R^9$=hydrogen atom, $R^{10}$=Glycine (4-phenyl-1-butanol) ester residue, $R^{11}$=Benzyloxy Group, i+j+k+m+n=21, b=273)

2.84 g of methoxy polyethylene glycol-polyglutamic acid block copolymer which has been produced according to the method described in International Publication Pamphlet No. 2006/1209144 and Compound 6 (1.72 g) obtained from Synthetic example 6 were dissolved in 50 mL of DMF, added with 0.54 mL of triethylamine, 0.05 g of DMAP, and 1.26 mL of DIPC at 25° C., and then stirred for 20 hours at 25° C. Subsequently, the precipitates that are obtained in the same manner as Compound 8 were dissolved at 5° C. in 70 mL of acetonitrile and 20 mL of water, passed through an ion exchange column (trade name: DOWEX 50($H^+$), manufactured by Dow Chemical Company, 10 mL), and then eluted with acetonitrile/water (5/1 (v/v), 30 mL). To the resulting eluted fraction, 130 mL of water was added and acetonitrile was distilled off under reduced pressure. Subsequently, Compound 11 (4.25 g) was obtained by freeze drying.

The content of aspartic acid f-benzyl ester-glycine (4-phenyl-1-butanol) ester bound to Compound 11 was calculated from the amount of benzyl alcohol which has been obtained in the same manner as Compound 8. As a result, the content of the bound aspartic acid β-benzyl ester-glycine (4-phenyl-1-butanol) ester was 36.3% (w/w), and the ratio of j compared to the total glutamic acid (i+j+k+m+n) was 95%. On the side chain of the remaining glutamic acid, isopropyl amino carbonyl isopropylamide group or hydroxy group was bonded.

Synthetic Example 12

Synthesis of Compound 1.2 (amide conjugate of a block copolymer consisting of methoxy polyethylene glycol moiety having molecular weight of 12,000 and polyglutamic acid moiety having polymerization number of 21 and aspartic acid β-benzyl ester n-butylamide: in general formula (III), $R^1$=Me, $R^2$=trimethylene group, $R^3$=Ac, $R^8$ and $R^9$=hydrogen atom, $R^{10}$=n-butyl Group, $R^{11}$=benzyloxy group, i+j+k+m+n=21, b=273)

2.92 g of methoxy polyethylene glycol-polyglutamic acid block copolymer which has been produced according to the method described in International Publication No. 2006/120914 and Compound 7 (1.24 g) obtained from Synthetic example 7 were dissolved in 52 mL of DMF, added with 0.55 mL of triethylamine, 0.05 g of DMAP, and 1.30 mL of DIPC at 25° C., and then stirred for 20 hours at 25° C. Subsequently, the precipitates that are obtained in the same manner as the Compound 8 were dissolved at 5° C. in 60 mL of acetonitrile and 15 mL of water, passed through an ion exchange column (trade name. DOWEX 50 ($H^+$), manufactured by Dow Chemical Company, 10 mL), and then eluted with acetonitrile/water (5/1 (v/v), 30 mL) To the resulting eluted fraction, 100 mL of water was added and acetonitrile was distilled off under reduced pressure. Subsequently, Compound 12 (3.89 g) was obtained by freeze drying.

The content of aspartic acid β-benzyl ester n-butylamide bound to Compound 12 was calculated from the amount of benzyl alcohol which has been obtained in the same manner as in the Compound 8. As a result, the content of the bound aspartic acid β-benzyl ester n-butylamide was 28.4% (w/w), and the ratio of j compared to the total glutamic acid (i+j+k+m+n) was 95%. On the side chain of the remaining glutamic acid, an isopropylamino carbonyl isopropylamide group or a hydroxy group was bonded.

Synthetic Example 13

Synthesis of Compound 13 (amide conjugate of a block copolymer consisting of methoxy polyethylene glycol moiety having molecular weight of 12,000 and polyglutamic acid moiety having polymerization number of 21 and aspartic acid β-benzyl ester glycine methyl ester and phenylalanine (4-phenyl-1-butanol) ester: in general formula (III), $R^1$=Me, $R^2$=trimethylene group, $R^3$=Ac, $R^7$=amino group of phenylalanine (4-phenyl-1-butanol) ester, $R^8$ and $R^9$=hydrogen atom, $R^{10}$=glycine methyl ester residue, $R^{11}$=benzyloxy group, i+j+k+m+n=21, b=273)

2.17 g of methoxy polyethylene glycol-polyglutamic acid block copolymer which has been produced according to the method described in International Publication Pamphlet No. 2006/120914 and Compound 2 (0.1 g) obtained from Synthetic example 2 and Compound 3 (0.87 g) obtained from Synthetic example 3 were dissolved in 38 mL of DMF, added with 0.41 mL of triethylamine, 0.04 g of DMAP, and 0.97 mL of DIPC at 25° C., and then stirred for 20 hours at 25° C. Subsequently, the precipitates that are obtained in the same manner as the Compound 8 were dissolved at 5° C. in 50 mL of acetonitrile and 13 mL of water, passed through an ion exchange column (trade name: DOWEX 50($H^+$), manufactured by Dow Chemical Company, 10 mL), and then eluted with acetonitrile/water (5/1 (v/v), 30 mL) To the resulting eluted fraction, 80 mL of water was added and acetonitrile was distilled off under reduced pressure. Subsequently, Compound 13 (2.9 g) was obtained by freeze drying.

The content of aspartic acid β-benzyl ester-glycine methyl ester bound to Compound 13 was calculated from the amount of benzyl alcohol which has been obtained in the same manner as in the Compound 8. As a result, the content of the bonded aspartic acid β-benzyl ester-glycine methyl ester was 26.3% (w/w), and the ratio of j compared to the total glutamic acid (i+j+k+m+n) was 84%. Further, 2 N-aqueous sodium hydroxide solution was added to Compound 13 stirred at 40° C. for 1 hour. The released 4-phenyl-1-butanol was analyzed by HPLC (high performance liquid chromatography), and the content of phenylalanine (4-phenyl-1-butanol) ester bound to Compound 13 was calculated from the amount of 4-phenyl-1-butanol obtained from the calibration curve established with commercially available 4-phenyl-1-butanol. As a result, the content of the bounded phenylalanine (4-phenyl-1-butanol) ester was 3.4% (w/w), and the ratio of m, which is a ratio of glutamic acid bound with the amino group of phenylalanine (4-phenyl-1-butanol) ester compared to the total glutamic acid (i+j+k+m+n), was 11%. On the side chain of the remaining glutamic acid, isopropylamino carbonyl isopropylamide group or hydroxy group was bonded.

Synthetic Example 14

Synthesis of Compound 14 (amide conjugate of a block copolymer consisting of methoxy polyethylene glycol moiety having molecular weight of 12,000 and polyglutamic acid moiety having polymerization number of 21 and aspartic acid-glycine methyl ester: in general formula (III), $R^1$=Me, $R^2$=trimethylene group, $R^3$=Ac, $R^8$ and $R^9$=hydrogen atom, $R^{10}$=glycine methyl ester residue, $R^{11}$=hydroxy group, i+j+k+m+n=21, b=273)

Compound 8 (2.73 g) obtained from Synthetic example 8 was dissolved in 68 mL of DMF, added with 0.27 g of 5% palladium carbon (moisture content of 50%), and hydrogenolyzed overnight at 25° C. 5% palladium carbon was filtered off and the filtrate was washed with 80 mL of ethyl acetate. 400 ml of heptane and 120 mL of ethyl acetate were added to the filtrate and stirred for 2 hours at room temperature. The precipitates were filtered and dried under vacuum to obtain Compound 14 (2.31 g).

Synthesis of Compound 15

Synthesis of Compound 1.5 (amide conjugate of a block copolymer consisting of methoxy polyethylene glycol moiety having molecular weight of 12,000 and polyglutamic acid moiety having polymerization number of 21 and aspartic acid-phenylalanine methyl ester: in general formula (III), $R^1$=Me, $R^2$=trimethylene group, $R^3$=Ac, $R^8$ and $R^9$=hydrogen atom, $R^{10}$=phenylalanine methyl ester residue, $R^{11}$=hydroxy group, i+j+k+m+n=21, b=273)

Compound 9 (4.51 g) obtained from Synthetic example 9 was dissolved in 113 mL of DMF, added with 0.45 g of 5% palladium carbon (moisture content of 50%), and hydrogenolyzed overnight at 25° C. Subsequently, Compound 15 (3.81 g) was obtained in the same manner as Compound 14.

Synthetic Example 16

Synthesis of Compound 16 (amide conjugate of a block copolymer consisting of methoxy polyethylene glycol moiety having molecular weight of 12,000 and polyglutamic acid moiety having polymerization number of 21 and aspartic acid-leucine methyl ester: in general formula (III), $R^1$=Me, $R^2$=trimethylene group, $R^3$=Ac, $R^8$ and $R^9$=hydrogen atom, $R^{10}$=leucine methyl ester residue, $R^{11}$=hydroxy group, i+j+k+m+n=21, b=273)

Compound 10 (4.21 g) obtained from Synthetic example 10 was dissolved in 105 mL DMF, added with 0.42 g of 5% palladium carbon (moisture content 50%), and hydrogenolyzed overnight at 25° C. Subsequently, Compound 16 (3.61 g) was obtained in the same manner as Compound 14.

Synthetic Example 17

Synthesis of Compound 17 (amide conjugate of a block copolymer consisting of methoxy polyethylene glycol moiety having molecular weight of 12,000 and polyglutamic acid moiety having polymerization number of 21 and aspartic acid-glycine (4-phenyl-1-butanol) ester: in general formula (III), $R^1$=Me, $R^2$=trimethylene group, $R^3$=Ac, $R^8$ and $R^9$=hydrogen atom, $R^{10}$=glycine (4-phenyl-1-butanol) ester residue, $R^{11}$=hydroxy group, i+j+k+m+n=21, b=273)

Compound 11 (4.20 g) obtained from Synthetic example 11 was dissolved in 105 mL of DMF, added with 0.42 g of 5% palladium carbon (moisture content of 50%), and hydrogenolyzed overnight at 25° C. Subsequently, Compound 17 (3.58 g) was obtained in the same manner as Compound 14.

Synthetic Example 18

Synthesis of Compound 18 (amide conjugate of a block copolymer consisting of methoxy polyethylene glycol moiety having molecular weight of 12,000 and polyglutamic acid moiety having polymerization number of 21 and aspartic acid n-butylamide: in general formula (III), $R^1$=Me, $R^2$=trimethylene group, $R^3$=Ac, $R^8$ and $R^9$=hydrogen atom, $R^{10}$=n-butyl group, $R^{11}$=hydroxy group, i+j+k+m+n=21, b=273)

Compound 12 (3.84 g) obtained from Synthetic example 12 was dissolved in 96 mL of DMF, added with 0.38 g of 5% palladium carbon (moisture content of 50%), and hydrogenolyzed overnight at 25° C. Subsequently, Compound 18 (3.29 g) was obtained in the same manner as Compound 14.

Synthetic Example 19

Synthesis of Compound 19 (amide conjugate of a block copolymer consisting of methoxy polyethylene glycol moiety having molecular weight of 12,000 and polyglutamic acid moiety having polymerization number of 21 and aspartic acid-glycine methyl ester and phenylalanine (4-phenyl-1-butanol) ester: in general formula (III), $R^1$=Me, $R^2$=trimethylene group, $R^3$=Ac, $R^7$=amino group of phenylalanine (4-phenyl-1-butanol) ester, $R^8$ and $R^9$=hydrogen atom, $R^{10}$=glycine methyl ester residue, $R^{11}$=hydroxy group, i+j+k+m+n=21, b=273)

Compound 13 (2.89 g) obtained from Synthetic example 13 was dissolved in 72 mL of DMF, added with 0.29 g of 5% palladium carbon (moisture content of 50%), and hydrogenolyzed overnight at 25° C. Subsequently, Compound 19 (2.48 g) was obtained in the same manner as Compound 14.

Example 1

Synthesis of Compound 20 (a polymer conjugate in which combretastatin A4 is ester-bonded to a block copolymer consisting of methoxy polyethylene glycol moiety having molecular weight of 12,000 and polyglutamic acid moiety having polymerization number of 21 through amide bond linker of aspartic acid-glycine methyl ester: in general formula (III), $R^1$=Me, $R^2$=trimethylene group, $R^3$=Ac, $R^8$ and $R^9$=hydrogen atom, $R^{10}$=glycine methyl ester residue, A=combretastatin residue, i+j+k+m+n=21, b=273)

Combretastatin A4 (0.13 g) which has been obtained according to the method described in J. Med. Chem., 38, 1666-1672 (1995) and Compound 14 (0.97 g) obtained from Synthetic example 14 were dissolved in 7 mL of DMF, added with 0.013 g of DMAP, and 0.32 mL of DIPC at 20° C., and then stirred for 20 hours at 20° C. To the reaction solution, 20 mL of ethyl acetate and 80 mL of diisopropyl ether were added and stirred for 2 hours at room temperature. Subsequently, the precipitates were filtered and washed with ethyl acetate/diisopropyl ether (1/4 (v/v), 20 mL). The resulting precipitates were dissolved at 5° C. in 30 mL of acetonitrile and 3 mL of water, passed through an ion exchange column (trade name: DOW 50($H^+$) manufactured by Dow Chemical Company, 3 mL), and then eluted with acetonitrile/water (10/(v/v), 20 mL). To the resulting eluted fraction, 100 mL of water was added and acetonitrile was distilled off under reduced pressure. Subsequently, Compound 20 (1.09 g) was obtained by freeze drying.

No free combretastatin A4 was detected from Compound 20. As a result of measuring the amount of unreacted combretastatin A4 in the reaction solution by HPLC, the content of combretastatin A4 in Compound 20 was 10.5% (w/w) and the ratio compared to the total glutamic acid (i+j+k+m+n) was 32%.

Gaussian distribution analysis was carried out for the aqueous solution (1 mg/ml) of Compound 20. As a result, it was found to be 18 nm (volume weighting). Thus, it was believed that Compound 20 formed a micelle in water.

Example 2

Synthesis of Compound 21 (a polymer conjugate in which combretastatin A4 is ester-bonded to a block copolymer consisting of methoxy polyethylene glycol moiety having molecular weight of 12,000 and polyglutamic acid moiety having polymerization number of 21 through amide bond linker of aspartic acid-phenylalanine methyl ester: in general formula (III), $R^1$=Me, $R^2$=trimethylene group, $R^3$=Ac, $R^8$ and $R^9$=hydrogen atom, $R^{10}$=phenylalanine methyl ester residue, A=combretastatin residue, i+j+k+m+n=21, b=273)

Combretastatin A4 (0.13 g) and Compound 15 (1.06 g) obtained from Synthetic example 15 were dissolved in 7 mL of DMF, added with 0.013 g of DMAP and 0.32 mL of DIPC at 20° C., and stirred for 20 hours at 20° C. Subsequently, Compound 21 (1.17 g) was obtained in the same manner as Compound 20.

No free combretastatin A4 was detected from Compound 21. As a result of measuring the amount of unreacted combretastatin A4 in the reaction solution by HPLC, the content of combretastatin A4 in Compound 21 was 11.0% (w/w) and the ratio i compared to the total glutamic acid (i+j+k+m+n) was 37%.

Gaussian distribution analysis was carried out for the aqueous solution (1 mg/ml) of Compound 21. As a result, it was found to be 33 nm (volume weighting). Thus, it was believed that Compound 21 formed a micelle in water.

Example 3 synthesis of compound 22 (a polymer conjugate in which combretastatin A4 is ester-bonded to a block copolymer consisting of methoxy polyethylene glycol moiety having molecular weight of 12,000 and polyglutamic acid moiety having polymerization number of 21 through amide bond linker of aspartic acid-leucine methyl ester: in general formula (III), $R^1$=Me, $R^2$=trimethylene group, $R^3$=Ac, $R^8$ and $R^9$=hydrogen atom, $R^{10}$=leucine methyl ester residue, A=combretastatin residue, i+j+k+m+n=21, b=273)

Combretastatin A4 (0.13 g) and Compound 16 (1.15 g) obtained from Synthetic example 16 were dissolved in 7 mL of DMF, added with 0.013 g of DMAP and 0.32 mL of DIPC at 20° C., and stirred for 20 hours at 20° C. Subsequently, Compound 22 (1.26 g) was obtained in the same manner as Compound 20.

No free combretastatin A4 was detected from Compound 22. As a result of measuring the amount of unreacted combretastatin A4 in the reaction solution by HPLC, the content of combretastatin A4 in Compound 22 was 10.3% (w/w) and the ratio compared to the total glutamic acid (i+j+k+m+n) was 32%.

Gaussian distribution analysis was carried out for the aqueous solution (1 mg/ml) of Compound 22. As a result, it was found to be 35 nm (volume weighting). Thus, it was believed that Compound 22 formed a micelle in water.

Example 4

Synthesis of Compound 23 (a polymer conjugate in which combretastatin A4 is ester-bonded to a block copolymer consisting of methoxy polyethylene glycol moiety having molecular weight of 12,000 and polyglutamic acid moiety having polymerization number of 21 through amide bond linker of aspartic acid-glycine (4-phenyl-1-butanol) ester: in general formula (III), $R^1$=Me, $R^2$=trimethylene group, $R^3$=Ac, $R^8$ and $R^9$=hydrogen atom, $R^{10}$=glycine (4-phenyl-1-butanol) ester residue, A=combretastatin residue, i+j+k+m+n=21, b=273)

Combretastatin A4 (0.13 g) and Compound 17 (1.07 g) obtained from Synthetic example 17 were dissolved in 7 mL of DMF, added with 0.013 g of DMAP and 0.32 mL of DIPC at 20° C., and stirred for 20 hours at 20° C. Subsequently, Compound 23 (1.17 g) was obtained in the same manner as Compound 20.

No free combretastatin A4 was detected from Compound 23. As a result of measuring the amount of unreacted combretastatin A4 in the reaction solution by HPLC, the content of combretastatin A4 in Compound 23 was 10.2% (w/w) and the ratio i compared to the total glutamic acid (i+j+k+m+n) was 35%.

Gaussian distribution analysis was carried out for the aqueous solution (1 mg/ml) of Compound 23. As a result, it was found to be 39 nm (volume weighting). Thus, it was believed that Compound 23 formed a micelle in water.

Example 5

Synthesis of Compound 24 (a polymer conjugate in which combretastatin A4 is ester-bonded to a block copolymer consisting of methoxy polyethylene glycol moiety having molecular weight of 12,000 and polyglutamic acid moiety having polymerization number of 21 through amide bond linker of aspartic acid n-butylamide: in general formula (III), $R^1$=Me, $R^2$=trimethylene group, $R^3$=Ac, $R^8$ and $R^9$=hydrogen atom, $R^{10}$=n-butyl group, A=combretastatin residue, i+j+k+m+n=21, b=273)

Combretastatin A4 (0.13 g) and Compound 18 (0.91 g) obtained from Synthetic example 18 were dissolved in 7 mL of DMF, added with 0.013 g of DMAP and 0.32 mL of DIPC at 20° C., and stirred for 20 hours at 20° C. Subsequently, Compound 24 (0.93 g) was obtained in the same manner as Compound 20.

No free combretastatin A4 was detected from Compound 24. As a result of measuring the amount of unreacted combretastatin A4 in the reaction solution by HPLC, the content of combretastatin A4 in Compound 24 was 12.7% (w/w) and the ratio i compared to the total glutamic acid (i+j+k+m+n) was 40%.

Gaussian distribution analysis was carried out for the aqueous solution (1 mg/ml) of Compound 24. As a result, it was found to be 16 nm (volume weighting). Thus, it was believed that Compound 24 formed a micelle in water.

Example 6

Synthesis of Compound 25 (a polymer conjugate in which combretastatin A4 is ester-bonded to a block copolymer consisting of methoxy polyethylene glycol moiety having molecular weight of 12,000 and polyglutamic acid moiety having polymerization number of 21 through amide bond linker of phenylalanine (4-phenyl-1-butanol) ester and aspartic acid-glycine methyl ester: in general formula (III), $R^1$=Me, $R^2$=trimethylene group, $R^3$=Ac, $R^7$=amino group of phenylalanine (4-phenyl-1-butanol) ester, $R^8$ and $R^9$=hydrogen atom, $R^{10}$=glycine methyl ester residue, A=combretastatin residue, i+j+k+m+n=21, b=273)

Combretastatin A4 (0.13 g) and Compound 19 (1.05 g) obtained from Synthetic example 19 were dissolved in 7 mL of DMF, added with 0.013 g of DMAP and 0.32 mL of DIPC at 20° C., and stirred for 20 hours at 20° C. Subsequently, Compound 25 (1.14 g) was obtained in the same manner as Compound 20.

No free combretastatin A4 was detected from Compound 25. As a result of measuring the amount of unreacted combretastatin A4 in the reaction solution by HPLC, the content of combretastatin A4 in Compound 25 was 9.9 (w/w) and the ratio compared to the total glutamic acid (i+j+k+m+n) was 31%.

Gaussian distribution analysis was carried out for the aqueous solution (1 mg/ml) of Compound 25. As a result, it was found to be 22 nm (volume weighting). Thus, it was believed that Compound 25 formed a micelle in water.

Example 7

Synthesis of Compound 26 (a polymer conjugate in which docetaxel is ester-bonded to a block copolymer consisting of methoxy polyethylene glycol moiety having molecular weight of 12,000 and polyglutamic acid moiety having polymerization number of 21 through amide bond linker of aspartic acid-glycine methyl ester: in general formula (III), $R^1$=Me, $R^2$=trimethylene group, $R^3$=Ac, $R^8$ and $R^9$=hydrogen atom, $R^{10}$=glycine methyl ester residue, A=docetaxel residue, i+j+k+m+n=21, b=273)

Commercially available docetaxel (0.13 g) and Compound 14 (0.45 g) obtained from Synthetic example 14 were dissolved in 3 mL of DMF, added with 0.006 g of DMAP, and 0.15 mL of DIPC at 20° C., and then stirred for 20 hours at 20° C. To the reaction solution, 4.5 mL of ethanol, 4.5 ml of ethyl acetate and 36 ml of diisopropyl ether were added and stirred for 2 hours at room temperature. Subsequently, the precipitates were filtered and washed with ethanol/diisopropyl ether (1/4 (v/v), 10 mL). The resulting precipitates were dissolved at 5° C. in 20 mL of acetonitrile and 2 mL of water, passed through an ion exchange column (trade name: DOWEX 50 ($H^+$), manufactured by Dow Chemical Company, 2 mL), and then eluted with acetonitrile/water (10/1 (v/v), 10 mL). To the resulting eluted fraction, 50 mL of water was added and acetonitrile was distilled off under reduced pressure. Subsequently, Compound 26 (0.54 g) was obtained by freeze drying.

No free docetaxel was detected from Compound 26. As a result of measuring the amount of unreacted docetaxel in the reaction solution by HPLC, the content of docetaxel in Compound 26 was 17.2% (w/w) and the ratio i compared to the total glutamic acid (i+j+k+m+n) was 22%.

Gaussian distribution analysis was carried out for the aqueous solution (1 mg/ml) of Compound 26. As a result, it was found to be 24 nm (volume weighting). Thus, it was believed that Compound 26 formed a micelle in water.

Example 8

Synthesis of Compound 27 (a polymer conjugate in which docetaxel is ester-bonded to a block copolymer consisting of methoxy polyethylene glycol moiety having molecular weight of 12,000 and polyglutamic acid moiety having polymerization number of 21 through amide bond linker of aspartic acid-phenylalanine methyl ester: in general formula (III), $R^1$=Me, $R^2$=trimethylene group, $R^3$=Ac, $R^8$ and $R^9$=hydrogen atom, $R^{10}$=phenylalanine methyl ester residue, A=docetaxel residue, i+j+k+m+n=21, b=273)

Docetaxel (0.13 g) and Compound 15 (0.48 g) obtained from Synthetic example 15 were dissolved in 3 mL of DMF, added with 0.006 g of DMAP and 0.15 mL of DIPC at 20° C., and stirred for hours at 20° C. Subsequently, Compound 27 (0.58 g) was obtained in the same manner as Compound 26.

No free docetaxel was detected from Compound 27. As a result of measuring the amount of unreacted docetaxel in the reaction solution by HPLC, the content of docetaxel in Compound 27 was 16.1% (w/w) and the ratio i compared to the total glutamic acid (i+j+k+m+n) was 23%.

Gaussian distribution analysis was carried out for the aqueous solution (1 mg/ml) of Compound 27. As a result, it was found to be 54 nm (volume weighting). Thus, it was believed that Compound 27 formed a micelle in water.

Example 9

Synthesis of Compound 28 (a polymer conjugate in which docetaxel is ester-bonded to a block copolymer consisting of methoxy polyethylene glycol moiety having molecular weight of 12,000 and polyglutamic acid moiety having polymerization number of 21 through amide bond linker of aspartic acid-leucine methyl ester: in general formula (III), $R^1$=Me, $R^2$=trimethylene group, $R^3$=Ac, $R^8$ and $R^9$=hydrogen atom, $R^{10}$=leucine methyl ester residue, A=docetaxel residue, i+j+k+m+n=21, b=273)

Commercially available docetaxel (0.13 g) and Compound 16 (0.52 g) obtained from Synthetic example 16 were dissolved in 3 mL of DMF, added with 0.006 g of DMAP and 0.15 mL of DIPC at 20° C., and stirred for 20 hours at 20° C. Subsequently, Compound 28 (0.64 g) was obtained in the same manner as Compound 26.

No free docetaxel was detected from Compound 28. As a result of measuring the amount of unreacted docetaxel in the reaction solution by HPLC, the content of docetaxel in Compound 28 was 17.2% (w/w) and the ratio i compared to the total glutamic acid (i+j+k+m+n) was 23%.

Gaussian distribution analysis was carried out for the aqueous solution (1 mg/ml) of Compound 28. As a result, it was found to be 0.36 nm (volume weighting). Thus, it was believed that Compound 28 formed a micelle in water.

Example 10

Synthesis of Compound 29 (a polymer conjugate in which docetaxel is ester-bonded to a block copolymer consisting of methoxy polyethylene glycol moiety having molecular weight of 12,000 and polyglutamic acid moiety having polymerization number of 21 through amide bond linker of aspartic acid-glycine (4-phenyl-1-butanol) ester: in general formula (III), $R^1$=Me, $R^2$=trimethylene group, $R^3$=Ac, $R^8$ and $R^9$=hydrogen atom, $R^{10}$=glycine (4-phenyl-1-butanol) ester residue, A=docetaxel residue, i+j+k+m+n=21, b=273)

Docetaxel (0.13 g) and Compound 17 (0.49 go) obtained from Synthetic example 17 were dissolved in 3 mL of DMF, added with 0.006 g of DMAP and 0.15 mL of DIPC at 20° C., and stirred for hours at 20° C. Subsequently, Compound 29 (0.58 g) was obtained in the same manner as Compound 26.

No free docetaxel was detected from Compound 29. As a result of measuring the amount of unreacted docetaxel in the reaction solution by HPLC, the content of docetaxel in Compound 29 was 17.3% (w/w) and the ratio i compared to the total glutamic acid (i+j+k+m+n) was 26%.

Gaussian distribution analysis was carried out for the aqueous solution (1 mg/ml) of Compound 29. As a result, it was found to be 31 nm (volume weighting). Thus, it was believed that Compound 29 formed a micelle in water.

Example 11

Synthesis of Compound 30 (a polymer conjugate in which docetaxel is ester-bonded to a block copolymer consisting of methoxy polyethylene glycol moiety having molecular weight of 12,000 and polyglutamic acid moiety having polymerization number of 21 through amide bond linker of phenylalanine (4-phenyl-1-butanol) ester, and aspartic acid-glycine methyl ester: in general formula (III), $R^1$=Me, $R^2$=trimethylene group, $R^3$=Ac, $R^7$=amino group of phenylalanine (4-phenyl-1-butanol) ester, $R^8$ and $R^9$=hydrogen atom, $R^{10}$=glycine methyl ester residue, A=docetaxel residue, i+j+k+m+n=21, b=273)

Docetaxel (0.13 g) and Compound 19 (0.48 g) obtained from Synthetic example 19 were dissolved in 3 mL of DMF, added with 0.006 g of DMAP and 0.15 mL of DIPC at 20° C., and stirred for hours at 20° C. Subsequently, Compound 30 (0.58 g) was obtained in the same manner as Compound 26.

No free docetaxel was detected from Compound 30. As a result of measuring the amount of unreacted docetaxel in the reaction solution by HPLC, the content of docetaxel in Compound 30 was 19.5% (w/w) and the ratio i compared to the total glutamic acid (i+j+k+m+n) was 27%.

Gaussian distribution analysis was carried out for the aqueous solution (1 mg/ml) of Compound 30. As a result, it was found to be 66 nm (volume weighting). Thus, it was believed that Compound 30 formed a micelle in water.

Example 12

Synthesis of Compound 31 (a polymer conjugate in which gemcitabine is bonded to a block copolymer consisting of methoxy polyethylene glycol moiety having molecular weight of 12,000 and polyglutamic acid moiety having polymerization number of 21 through amide bond linker of aspartic acid-phenylalanine methyl ester: in general formula (III), $R^1$=Me, $R^2$=trimethylene group, $R^3$=Ac, $R^8$ and $R^9$=hydrogen atom, $R^{10}$=phenylalanine methyl ester residue, A=gemcitabine residue, i+j+k+m+n=21, b=273)

Commercially available gemcitabine (0.13 g) and Compound 0.15 (1.02 g) obtained from Synthetic example 1.5 were dissolved in 7 mL of DMF, added with 0.012 g of DMAP, and 0.31 mL of DIPC at 20° C., and then stirred for 20 hours at 20° C. To the reaction solution, 20 mL of ethanol and 30 mL of diisopropyl ether were added and stirred for 2 hours at room temperature. Subsequently, the precipitates were filtered and washed with ethanol/diisopropyl ether (1/4 (v/v) 30 mL). The resulting precipitates were dissolved at 5° in 30 mL of acetonitrile and 6 mL of water, and passed through an ion exchange column (trade name: DOWEX 50 (H⁺), manufactured by Dow Chemical Company, 3 mL), and then eluted with acetonitrile/water (10/1 (v/v), 30 mL). To the resulting eluted fraction, 110 mL of water was added and acetonitrile was distilled off under reduced pressure. Subsequently, Compound 31 (1.13 g) was obtained by freeze drying.

No free gemcitabine was detected from Compound 31. As a result of measuring the amount of unreacted gemcitabine in the reaction solution by HPLC, the content of gemcitabine in Compound 31 was 10.0% (w/w) and the ratio i compared to the total glutamic acid (i+j+k+m+n) was 35%.

Gaussian distribution analysis was carried out for the aqueous solution (1 mg/ml) of Compound 31. As a result, it was found to be 20 nm (volume weighting). Thus, it was believed that Compound 31 formed a micelle in water.

Example 13

Synthesis of Compound 32 (a polymer conjugate in which etoposide is ester-bonded to a block copolymer consisting of methoxy polyethylene glycol moiety having molecular weight of 12,000 and polyglutamic acid moiety having polymerization number of 21 through amide bond linker of aspartic acid-glycine (4-phenyl-1-butanol) ester: in general formula (III), $R^1$=Me, $R^2$=trimethylene group, $R^3$=Ac, $R^8$ and $R^9$=hydrogen atom, $R^{10}$=glycine (4-phenyl-1-butanol) ester residue, A=etoposide residue, i+j+k+m+n=21, b=273)

Commercially available etoposide (0.045 g) and Compound 17 (0.2 g) obtained from Synthetic example 17 were dissolved in 1.3 mL of DMF, added with 0.002 g of DMAP, and 0.06 mL of DIPC at 20° C., and then stirred for 20 hours at 20° C. To the reaction solution, 4 mL of ethyl acetate and 16 mL of diisopropyl ether were added and stirred for 2 hours at room temperature. Subsequently, the precipitates were filtered and washed with ethyl acetate/diisopropyl ether (1/4 (v/v), 5 mL). The resulting precipitates were dissolved at 5° C. in 12 mL of acetonitrile and 2 ml of water, passed through an ion exchange column (trade name: DOWEX 50(1H), manufactured by Dow Chemical Company, 0.5 mL), and then eluted with acetonitrile/water (10/1 (v/v), 2 mL). To the resulting eluted fraction, 12 mL of water was added and acetonitrile was distilled off under reduced pressure. Subsequently, Compound 32 (0.233 g) was obtained by freeze drying.

No free etoposide was detected from Compound 32. As a result of measuring the amount of unreacted etoposide in the reaction solution by HPLC, the content of etoposide in Compound 32 was 15.9% (w/w) and the ratio i compared to the total glutamic acid (i+j+k+m+n) was 32%.

Gaussian distribution analysis was carried out for the aqueous solution (1 mg/ml) of Compound 32. As a result, it was found to be 42 nm (volume weighting). Thus, it was believed that Compound 32 formed a micelle in water.

Example 14

Synthesis of Compound 33 (a polymer conjugate in which prednisolone is ester-bonded to a block copolymer consisting of methoxy polyethylene glycol moiety having molecular weight of 12,000 and polyglutamic acid moiety having polymerization number of 21 through amide bond linker of aspartic acid-glycine (4-phenyl-1-butanol) ester: in general formula (III), $R^1$=Me, $R^2$=trimethylene group, $R^3$=Ac, $R^8$ and $R^9$=hydrogen atom, $R^{10}$=glycine (4-phenyl-1-butanol) ester residue, A=prednisolone residue, i+j+k+m+n<21, b=273)

Commercially available prednisolone (0.048 g) and Compound 17 (0.2 g) obtained from Synthetic example 17 were dissolved in 1.3 mL of DMF, added with 0.002 g of DMAP, and 0.06 mL of DIPC at 20° C., and then stirred for 20 hours at 20° C. To the reaction solution, 4 mL of ethanol and 166 mL of diisopropyl ether were added and stirred for 2 hours at room temperature. Subsequently, the precipitates were filtered and washed with ethanol/diisopropyl ether (1/4 (v/v), mL). The resulting precipitates were dissolved at 5° C. in 12 mL of acetonitrile and 2 mL of water, passed through an ion exchange column (trade name: DOWEX 50 (H⁺), manufactured by Dow Chemical Company, 0.5 mL), and then eluted with acetonitrile/water (10/1 (v/v), 2 mL). To the resulting eluted fraction, 12 mL of water was added and acetonitrile was distilled off under reduced pressure. Subsequently, Compound 33 (0.239 g) was obtained by freeze drying.

No free prednisolone was detected from Compound 33. As a result of measuring the amount of unreacted prednisolone in the reaction solution by HPLC, the content of prednisolone in Compound 33 was 18.1% (w/w) and the ratio i compared to the total glutamic acid (i+j+k+m+n) was 60%.

Gaussian distribution analysis was carried out for the aqueous solution (1 mg/ml) of Compound 33. As a result, it was found to be 50 nm (volume weighting). Thus, it was believed that Compound 33 formed a micelle in water.

Example 15

Synthesis of Compound 34 (a polymer conjugate in which paclitaxel is ester-bonded to a block copolymer consisting of methoxy polyethylene glycol moiety having molecular weight of 12,000 and polyglutamic acid moiety having polymerization number of 21 through amide bond linker of phenylalanine (4-phenyl-1-butanol) ester and aspartic acid-glycine methyl ester: in general formula (III), $R^1$=Me, $R^2$=trimethylene group, $R^3$=Ac, $R^7$=amino group of phenylalanine (4-phenyl-1-butanol) ester, $R^8$ and $R^9$=hydrogen atom, $R^{10}$=glycine methyl ester residue, A=paclitaxel residue, i+j+k+m+n=21, b=273)

Commercially available paclitaxel (0.029 g) and Compound 19 (0.10 g) obtained from Synthetic example 19 were dissolved in 0.7 mL DMF, added with 0.0012 g of DMAP, and 0.031 mL of DIPC at 20° C., and then stirred for 20 hours at 20° C. To the reaction solution, 2 mL of ethanol and 8 mL of diisopropyl ether were added and stirred for 2 hours at room temperature. Subsequently, the precipitates were filtered and washed with ethanol/diisopropyl ether (1/4 (v/v), 3 mL). The resulting precipitates were dissolved at 5° C. in 6 mL of acetonitrile and 1.5 mL of water, passed through an ion exchange column (trade name: DOWEX 50 (H$^+$), manufactured by Dow Chemical Company, 0.5 mL), and then eluted with acetonitrile/water (10/1 (v/v), 6 mL) To the resulting eluted fraction, 12 mL of water was added and acetonitrile was distilled off under reduced pressure. Subsequently, Compound 34 (0.121 g) was obtained by freeze drying.

No free paclitaxel was detected from Compound 34. As a result of measuring the amount of unreacted paclitaxel in the reaction solution by HPLC, the content of paclitaxel in Compound 34 was 22.0% (w/w) and the ratio i compared to the total glutamic acid (i+j+k+m+n) was 34%.

Gaussian distribution analysis was carried out for the aqueous solution (1 mg/ml) of Compound 34. As a result, it was found to be 39 nm (volume weighting). Thus, it was believed that Compound 34 formed a micelle in water.

Example 16

Synthesis of Compound 35 (a polymer conjugate in which adenosine is ester-bonded to a block copolymer consisting of methoxy polyethylene glycol moiety having molecular weight of 12,000 and polyglutamic acid moiety having polymerization number of 21 through amide bond linker of aspartic acid-phenylalanine methyl ester: in general formula (III), $R^1$=Me, $R^2$=trimethylene group, $R^3$=Ac, $R^8$ and $R^9$=hydrogen atom, $R^{10}$=phenylalanine methyl ester residue, A=adenosine residue, i+j+k+m+n=21, b=273)

Commercially available adenosine (0.0123 g) and Compound 15 (0.119 g) obtained from Synthetic example 15 were dissolved in 0.8 mL of DMF, added with 0.0014 g of DMAP, and 0.036 mL of DIPC at 20° C., and then stirred for 20 hours at 20° C. To the reaction solution, 2.3 ml of ethanol and 9.2 mL of diisopropyl ether were added and stirred for 2 hours at room temperature. Subsequently, the precipitates were filtered and washed with ethanol/diisopropyl ether (1/4 (v/v), 3 mL). The resulting precipitates were dissolved at 5° C. in 6 ml of acetonitrile and 1.5 mL of water, passed through an ion exchange column (trade name: DOWEX 50 (—H), manufactured by Dow Chemical Company, 0.5 mL), and then eluted with acetonitrile/water (10/1 (v/v), 6 mL) To the resulting eluted fraction, 12 mL of water was added and acetonitrile was distilled off under reduced pressure. Subsequently, Compound 35 (0.127 g) was obtained by freeze drying.

No free adenosine was detected from Compound 35. As a result of measuring the amount of unreacted adenosine in the reaction solution by HPLC, the content of adenosine in Compound was 8.4% (w/w) and the ratio i compared t to the total glutamic acid (i+j+k+m+n) was 35%.

Gaussian distribution analysis was carried out for the aqueous solution (1 mg/ml) of Compound 35. As a result, it was found to be 29 nm (volume weighting). Thus, it was believed that Compound 35 formed a micelle in water.

Example 17

Synthesis of Compound 36 (a polymer conjugate in which capecitabine is bonded to a block copolymer consisting of methoxy polyethylene glycol moiety having molecular weight of 12,000 and polyglutamic acid moiety having polymerization number of 21 through amide bond linker of aspartic acid-phenylalanine methyl ester: in general formula (III), $R^1$=Me, $R^2$=trimethylene group, $R^3$=Ac, $R^8$ and $R^9$=hydrogen atom, $R^{10}$=phenylalanine methyl ester residue, A=capecitabine residue, i+j+k+m+n=21, b=273)

Commercially available capecitabine (0.0138 g) and Compound 15 (0.099 g) obtained from Synthetic example 15 were dissolved in 0.6 mL of DMF, added with 0.0017 g of DMAP, and 0.03 mL of DIPC at 20° C., and then stirred for 20 hours at 20° C. To the reaction solution, 2 mL of ethanol and 8 mL of diisopropyl ether were added and stirred for 2 hours at room temperature. Subsequently, the precipitates were filtered and washed with ethanol/diisopropyl ether (1/4 (v/v), 3 mL). The resulting precipitates were dissolved at 5° C. in 4 mL of acetonitrile and 1 mL of water, passed through an ion exchange column (trade name: DOWEX 50 (H$^+$), manufactured by Dow Chemical Company, 0.2 mL), and then eluted with acetonitrile/water (10/1 (v/v), 6 mL). To the resulting eluted fraction, 11 mL of water was added and acetonitrile was distilled off under reduced pressure. Subsequently, Compound 36 (0.112 g) was obtained by freeze drying.

No free capecitabine was detected from Compound 36. As a result of measuring the amount of unreacted capecitabine in the reaction solution by HPLC, the content of capecitabine in Compound 36 was 11.4% (w/w) and the ratio i compared to the total glutamic acid (i+j+k+m+n) was 37%.

Gaussian distribution analysis was carried out for the aqueous solution (1 mg/ml) of Compound 36. As a result, it was found to be 43 nm (volume weighting). Thus, it was believed that Compound 36 formed a micelle in water.

Example 18

Synthesis of Compound 37 (a polymer conjugate in which capecitabine is ester-bonded to a block copolymer consisting of methoxy polyethylene glycol moiety having molecular weight of 12,000 and polyglutamic acid moiety having polymerization number of 21 through amide bond linker of aspartic acid-glycine (4-phenyl-1-butanol) ester: in general formula (III), $R^1$=Me, $R^2$=trimethylene group, $R^3$=Ac, $R^8$ and $R^9$=hydrogen atom, $R^{10}$=glycine (4-phenyl-1-butanol) ester residue, A=capecitabine residue, i+j+k+m+n=21, b=273)

Commercially available capecitabine (0.014 g) and Compound 17 (0.1 g) obtained from Synthetic example 17 were dissolved in 0.6 mL of DMF, added with 0.001 g of DMAP, and 0.03 mL of DIPC at 20° C., and then stirred for 20 hours at 20° C. To the reaction solution, 2 mL of ethanol and 8 mL of diisopropyl ether were added and stirred for 2 hours at room temperature Subsequently, the precipitates were filtered and washed with ethanol/diisopropyl ether (1/4 (v/v), 3 mL). The resulting precipitates were dissolved at 5° C. in 4 mL of acetonitrile and 1 mL of water, passed through an ion exchange column (trade name: DOWEX 50 (H$^+$), manufactured by Dow Chemical Company, 0.2 mL), and then eluted with acetonitrile/water (10/1 (v/v), 6 mL). To the resulting eluted fraction, 11 mL of water was added and acetonitrile was distilled off under reduced pressure. Subsequently, Compound 37 (0.111 g) was obtained by freeze drying.

No free capecitabine was detected from Compound 37. As a result of measuring the amount of unreacted capecitabine in the reaction solution by HPLC, the content of capecitabine in Compound 37 was 10.9% (w/w) and the ratio i compared to the total glutamic acid (i+j+k+m+n) was 35%.

Gaussian distribution analysis was carried out for the aqueous solution (1 m/ml) of Compound 37. As a result, it was found to be 55 nm (volume weighting). Thus, it was believed that Compound 37 formed a micelle in water.

Test Example 1

Drug release from combretastatin a4 conjugate in the absence of enzymes

Compound 20 to Compound 25 and a combretastatin conjugate of polyethylene glycol-polyglutamic acid block copolymer (PEG-Glu-CA4) and a combretastatin conjugate of polyethylene glycol-polyaspartic acid block copolymer (PEG-Asp-CA4) as a comparative compound produced according to the method of International Publication No. 2008/10463 were each dissolved in a concentration of 1 mg/ml in PBS (phosphate buffered physiological saline, pH: 7.1), and incubated at 37° C. Combretastatin A4 released from the polymer conjugate was analyzed and quantified by HPLC in comparison with a calibration curve. The ratio of the quantified value to the total amount of the drug determined from the content of the drug in the polymer conjugate is shown in FIG. 1.

As is clear from FIG. 1, it shows that the polymer conjugates (Compound 20 to Compound 25) according to the invention release combretastatin A4 even in the absence of hydrolyzing enzymes. For all compounds tested, the release rate was faster than PEG-Glu-CA4. Further, the release rate could be significantly changed according to the difference in $R^{10}$ substituent bound to aspartic acid. These results suggest that the polymer conjugate of the invention has an excellent ability of controlling drug release rate.

Test Example 2

Drug release from docetaxel conjugate in the absence of enzymes

Compound 26 to Compound 30 and a docetaxel conjugate of polyethylene glycol-polyaspartic acid block copolymer (PEG-Asp-DTX) as a comparative compound produced according to the method of International Publication Pamphlet No. 2007/1111211 were each dissolved in a concentration of 1 mg/ml in PBS (phosphate buffered physiological saline, pH: 7.1), and incubated at 37° C. Docetaxel released from the polymer conjugate was analyzed and quantified by HPLC in comparison with a calibration curve. The ratio of the quantified value to the total amount of the drug determined from the content of the drug in the polymer conjugate is shown in FIG. 2.

Figure 2:
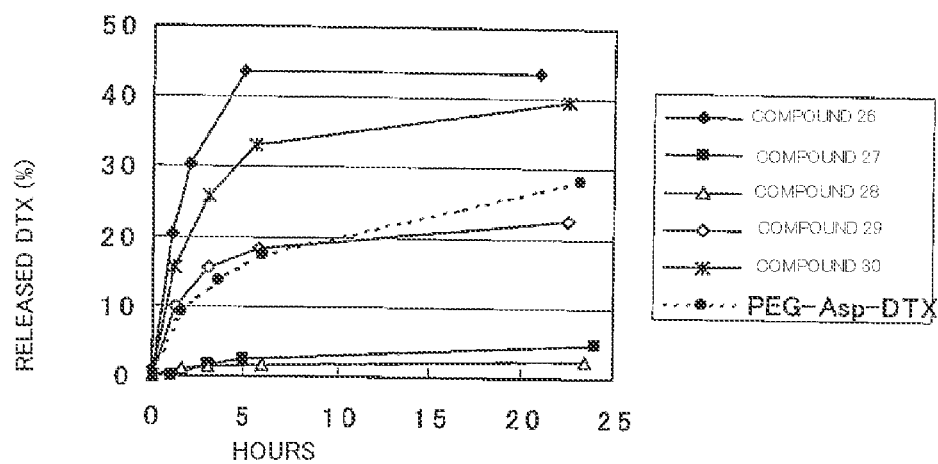
FIG. 2 illustrates the ratio of the amount of docetaxel (DTX) released from Compound 26 to 30 of the present Examples and the comparative compound (PEG-Asp-DTX), based on the total amounts of bound docetaxel in PBS solution (pH 7.1) at 37° C.

As is clear from FIG. 2, for the polymer conjugates according to the invention, the release rate could be significantly changed based on the $R^{10}$ substituent bound to aspartic acid. In particular, Compound 26 and Compound 30 could release docetaxel faster than PEG-Asp-DTX. These results suggest that the polymer conjugate of the invention has an excellent ability of controlling the drug release rate.

Test Example 3

Drug release from gemcitabine, etoposide, prednisolone, paclitaxel, or adenosine-bound polymer conjugate in the absence of enzymes Each of Compound 31 (gemcitabine conjugate), Compound 32 (etoposide conjugate), Compound 33 (prednisolone conjugate), Compound 34 (paclitaxel conjugate), and Compound 35 (adenosine conjugate) was dissolved in a concentration of 1 mg/ml in PBS (phosphate buffered physiological saline, pH: 7.1), and incubated at 37° C. Each drug released from the polymer conjugate was analyzed and quantified by HPLC in comparison with a calibration curve. The ratio of the quantified value to the total amount of the drug determined from the content of the drug in the polymer conjugate is shown in FIG. 3.

Figure 3:
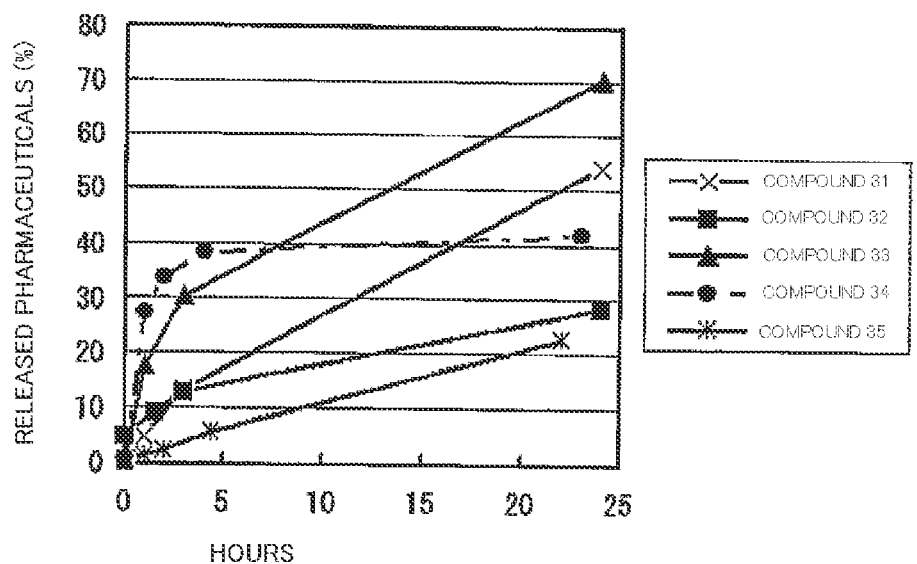
FIG. 3 illustrates the ratio of the amount of each pharmaceutical preparation released from Compound 31 to 35 of the present Examples, based on the total amounts of each bound pharmaceutical preparation in PBS solution (pH 7.1) at 37° C.

As is clear from FIG. 3, it shows that the polymer conjugate of physiologically active substance according to the invention could release the physiologically active substance even without a hydrolyzing enzyme.

Test Example 4

Drug release from capecitabine-bound polymer conjugate in the absence of enzymes Compound 36 and Compound 37 were each dissolved in a concentration of 1 mg/ml in PBS (phosphate buffered physiological saline, pH: 7.1), and incubated at 37° C. Each drug released from the polymer conjugate was analyzed and quantified by HPLC in comparison with a calibration curve. The ratio of the quantified value to the total amount of the drug determined from the content of the drug in the polymer conjugate is shown in FIG. 4.

Figure 4:
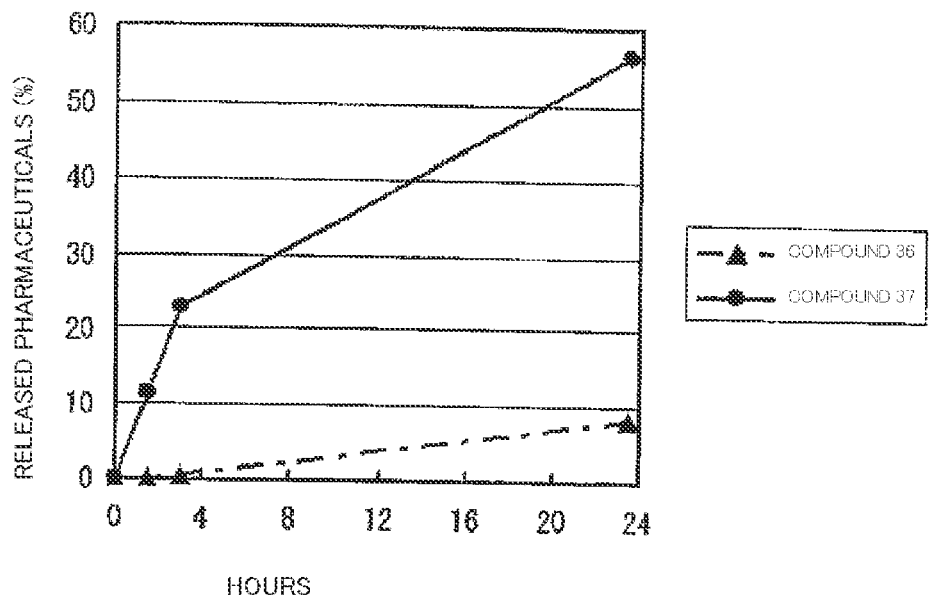
FIG. 4 illustrates the ratio of the amount of capecitabine released from Compound 36 and 37 of the present Examples, based on the total amounts of bound capecitabine in PBS solution (pH 7.1) at 37° C.

As is clear from FIG. 4, it shows that the polymer conjugate of physiologically active substance according to the invention could release the physiologically active substance even without a hydrolyzing enzyme. It also shows that the release rate could be controlled by modifying $R^{10}$.

Test Example 5

Antitumor activity test for combretastatin A4 conjugate

Mouse colon cancer, Colon 26, maintained by serial subcutaneous subculture in mice, was minced into about 2-mm cubic fragments, and the fragments were subcutaneously transplanted on the dorsal part of female CDF1 mice with a trocar. Eight days after the tumor transplantation, the polymer conjugate according to the invention (Compound 22) or a control drug (combretastatin A4 phosphate ester; CA4P, PEG-Glu-CA4 or PEG-Asp-CA4) was each administered once into the mouse tail vein in a way such that each mouse received the same dose per body weight in terms of combretastatin A4. Each compound was dissolved in a 5% aqueous glucose solution and used.

After the administration, the major axis (L mm) and the minor axis (W mm) of the tumor were measured using a caliper, and the tumor volume was calculated by the formula $(L \times W^2)/2$. Table 1 shows the relative tumor volume based on the tumor volume of a non-treatment group (i.e. control).

TABLE 1

| | | Days after administration (day) | | | | |
|---|---|---|---|---|---|---|
| | Dose | 0 | 2 | 4 | 6 | 8 |
| Compound 22 | 50 mg/kg | 1.00 | 0.68 | 0.19 | 0.12 | 0.24 |
| | 25 mg/kg | 1.00 | 0.77 | 0.42 | 0.54 | 0.41 |
| PEG-Glu-CA4 | 50 mg/kg | 1.00 | 0.59 | 0.15 | 0.10 | 0.11 |
| | 25 mg/kg | 1.00 | 1.02 | 0.83 | 0.94 | 0.86 |
| PEG-Asp-CA4 | 25 mg/kg | 1.00 | 0.38 | 0.43 | 0.56 | 0.78 |
| | 12.5 mg/kg | 1.00 | 0.50 | 0.65 | 0.54 | 0.66 |
| CA4P | 200 mg/kg | 1.00 | 0.72 | 0.82 | 0.80 | 0.80 |

Test Example 6

Effect of combretastatin A4 conjugate on heart muscle

Combretastatins are known to have a side effect of causing a myocardial damage. As such, by following a change in efficacy of creatinine phosphokinase (CPK) that is released into blood when enzymes abundantly present in heart muscles or neurons are damaged, the degree of side effect of the compounds according to the invention was compared to those of known compounds.

To a non-treated female CDF1 mouse, Compound 22 as a compound of the invention and CA4P, PEG-Glu-CA4, and PEG-Asp-CA4 as a comparative compound were each administered once into the mouse tail vein. Six hours and 24 hours after the administration, three animals per each group were anesthetized with ether and blood was taken from abdominal aorta. Creatinine phosphokinase (CPK) contained in plasma was measured. Change in average efficacy (IU/L) was shown in Table 2.

TABLE 2

|  | Dose | Hours after administration | |
|---|---|---|---|
|  |  | 6 hours | 24 hours |
| Compound 22 | 50 mg/kg | 300-400 | ≤200 |
|  | 25 mg/kg | ≤200 | ≤200 |
| PEG-Glu-CA4 | 50 mg/kg | 300-400 | 500-600 |
|  | 25 mg/kg | ≤200 | ≤200 |
| PEG-Asp-CA4 | 25 mg/kg | 400-500 | ≤200 |
|  | 12.5 mg/kg | 400-500 | ≤200 |
| CA4P | 200 mg/kg | 400-500 | ≤200 |

As is clear from Table 1 and Table 2, it shows that the polymer conjugate of the invention (Compound 22) exhibited an antitumor activity at dose of 25 mg/kg without having any increase in CPK, Much stronger antitumor activity was obtained from the dose of 50 mg/kg compared to 25 mg/kg. Although there was an increase in CPK after 6 hours, it was a transient increase as CPK was recovered to normal value after 24 hours.

On the other hand, combretastatin A4 phosphate ester as a control drug showed a weak antitumor activity even though a CPK increase was significant at dose of 200 mg/kg.

PEG-Glu-CA4 showed a strong antitumor activity at dose of 50 mg/kg but CPK remained at high level with no recovery even after 24 hours. It showed no antitumor activity at dose of 25 mg/kg.

PEG-Asp-CA4 at dose of 12.5 mg/kg showed an antitumor activity that was close to the activity of Compound 22 at dose of 25 mg/kg. However, CPK was increased even at such dose, and therefore the CPK increase and the antitumor activity cannot be separated from each other.

Test Example 7

Antitumor activity test for docetaxel conjugate

Mouse colon cancer, Colon 26, maintained by serial subcutaneous subculture in mice, was minced into about 2-mm cubic fragments, and the fragments were subcutaneously transplanted on the dorsal part of female CDF1 mice with a trocar. Eight days after the tumor transplantation, the polymer conjugate according to the invention (Compound 30) or a control drug (docetaxel; DTX or PEG-Asp-DTX) was each administered once into the mouse tail vein in a way such that each mouse received the same dose per body weight in terms of docetaxel. Docetaxel was dissolved in anhydrous ethanol and cremophor (manufactured by Sigma Corporation), and diluted with physiological saline at the time of use. Other compounds were dissolved in a 5% aqueous glucose solution for injection and used. After the administration, the major axis (L mm) and the minor axis (W mm) of the tumor were measured using a caliper, and the tumor volume was calculated by the formula $(L \times W^2)/2$. Table 3 shows the relative tumor volume based on the tumor volume of a non-treatment group (i.e. control).

TABLE 3

|  |  | Days after administration (day) | | | | |
|---|---|---|---|---|---|---|
| Dose |  | 0 | 3 | 5 | 9 | 12 |
| Compound 30 | 100 mg/kg | 1.00 | 0.36 | 0.16 | 0.03 | 0.05 |
|  | 50 mg/kg | 1.00 | 0.50 | 0.25 | 0.07 | 0.13 |
| PEG-Asp-DTX | 100 mg/kg | 1.00 | 0.48 | 0.25 | 0.06 | 0.07 |
|  | 50 mg/kg | 1.00 | 0.61 | 0.52 | 0.45 | 0.44 |
| DTX | 100 mg/kg | 1.00 | 0.50 | 0.32 | 0.37 | 0.35 |

As is clear from Table 3, it shows that the polymer conjugate of the invention (Compound 30) exhibited stronger antitumor activity than docetaxel even when the administered dose was only half of docetaxel (i.e. 50 mg/kg). Much stronger antitumor activity was obtained from the dose of 100 mg/kg.

On the other hard, the antitumor activity of PEG-Asp-DTX as a control drug was the same or less than that of DTX when PEG-Asp-DTX was administered with a dose of 50 mg/kg, although it showed a strong antitumor activity at dose of 100 mg/kg.

The invention claimed is:

1. A polymer conjugate of a physiologically active substance, comprising a block copolymer of a polyethylene glycol moiety and a polyglutamic acid moiety, in which a substituent bound to the physiologically active substance is linked to at least one of the side-chain carboxy groups of the block copolymer via an amide bond, and the physiologically active substance is directly bonded to the side-chain carboxy groups of the block copolymer, wherein the polymer conjugate is a compound represented by general formula (III)

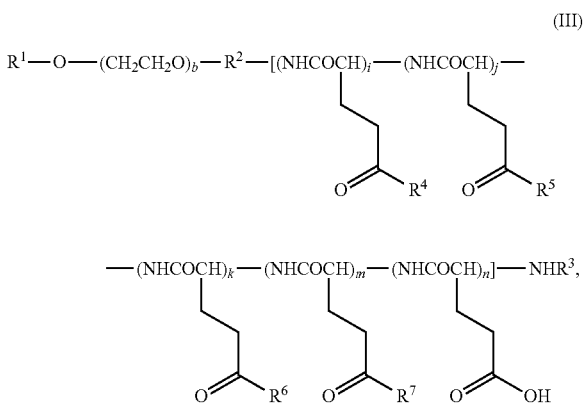

wherein $R^1$ represents hydrogen atom or (C1-C6)alkyl group, $R^2$ represents a linking group, $R^3$ represents hydrogen atom or (C1-C6)acyl group, $R^4$ represents a substituent represented by general formula (I) or general formula (II)

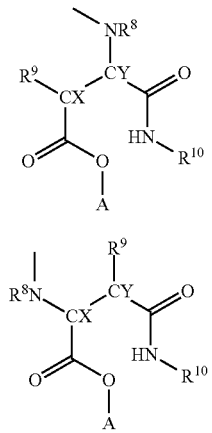

in which $R^8$ and $R^9$ each independently represent a hydrogen atom or (C1-C6)alkyl group which may optionally have a substituent, $R^{10}$ represents hydrogen atom, (C1-C40)alkyl group which may optionally have a substituent, (C1-C40)aralkyl group which may optionally have a substituent, an aromatic group which may optionally have a substituent, an amino acid residue having a protected carboxy group, or a sugar residue which may optionally have a substituent, CX—CY represents CH—CH or C=C (double bond), and A represents a residue obtained by removing, from the physiologically active substance having one or more hydroxy groups, one of the one or more hydroxy groups, $R^5$ represents a substituent represented by general formula (IV) or general formula (V)

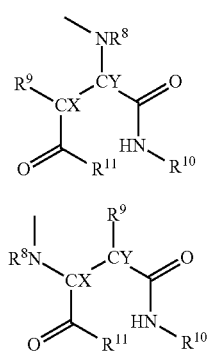

in which $R^8$, $R^9$, $R^{10}$, and CX—CY have the same meanings as above, $R^{11}$ represents one or more substituents selected from a group consisting of hydroxy group, an aromatic amino group which may optionally have a substituent, (C1-C30)alkoxy group which may optionally have a substituent, (C1-C30)aralkyloxy group which may optionally have a substituent, (C1-C30)alkylamino group which may optionally have a substituent, di(C1-C30)alkylamino group which may optionally have a substituent, an amino acid having a protected carboxy group, and $NR^{12}CONHR^{13}$, wherein $R^{12}$ and $R^{13}$, which may be the same or different from each other, represent (C3-C6)cyclic alkyl group, or (C1-C5)alkyl group which may optionally be substituted with a tertiary amino group, $R^6$ represents a substituent represented by general formula (VI)

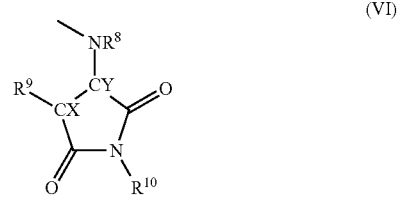

in which $R^8$, $R^9$, $R^{10}$, and CX—CY have the same meanings as above, $R^7$ represents a substituent selected from a group consisting of (C1-C30)alkoxy group, (C1-C30)aralkyloxy group, (C1-C30)alkylamino group, di(C1-C30)alkylamino group, an amino acid having a protected carboxy group, and $NR^{12}CONHR^{13}$, wherein $R^{12}$ and $R^{13}$, which may be the same or different from each other, represent (C3-C6)cyclic alkyl group, or (C1-C5)alkyl group which may optionally be substituted with a tertiary amino group, b is an integer from 5 to 11,500, i is an integer from 1 to 200, j, k, m, and n each represent an integer from 0 to 200 with the proviso that i+j+k+m+n represents an integer from 2 to 200.

2. The polymer conjugate of a physiologically active substance according to claim 1, in which $R^1$ is (C1-C3)alkyl group, $R^2$ is (C2-C6)alkylene group, $R^3$ is (C1-C3)acyl group, b is an integer from 100 to 300, i is an integer from 1 to 90, and j, k, m, and n each represent an integer from 0 to 90 with the proviso that i+j+k+m+n is an integer from 6 to 90.

3. The polymer conjugate of a physiologically active substance according to claim 2, in which $R^1$ is methyl group, $R^2$ is trimethylene group, $R^3$ is acetyl group, $R^8$ and $R^9$ in $R^4$, $R^5$ and $R^6$ are all hydrogen atoms, and CX—CY is CH—CH.

4. The polymer conjugate of a physiologically active substance according to any one of claims 1, 2 or 3, in which the physiologically active substance having one or more hydroxy groups is an anticancer agent.

5. The polymer conjugate of a physiologically active substance according to claim 4, in which the anticancer agent is taxoids.

6. The polymer conjugate of a physiologically active substance according to claim 5, in which the taxoids are paclitaxel or docetaxel.

7. The polymer conjugate of a physiologically active substance according to claim 4, in which the anticancer agent is podophyllotoxins.

8. The polymer conjugate of a physiologically active substance according to claim 7, in which the podophyllotoxins are podophyllotoxin, etoposide, or teniposide.

9. The polymer conjugate of a physiologically active substance according to claim 4, in which the anticancer agent is combretastatins.

10. The polymer conjugate of a physiologically active substance according to claim 9, in which the combretastatins are combretastatin A1 or combretastatin A4.

11. The polymer conjugate of a physiologically active substance according to claim 4, in which the anticancer agent is a nucleic acid-based anticancer agent.

12. The polymer conjugate of a physiologically active substance according to claim 11, in which the nucleic acid-based anticancer agent is gemcitabine, capecitabine, doxifluridine, cytarabine, or 3'-ethynylcytidine.

13. The polymer conjugate of a physiologically active substance according to claim 4, in which the anticancer agent is camptothecin or derivative thereof.

14. The polymer conjugate of a physiologically active substance according to claim 4, in which the anticancer agent is doxorubicin, amrubicin, or aclacinomycin.

15. The polymer conjugate of a physiologically active substance according to claim 1, 2 or 3, in which the physiologically active substance having the one or more hydroxy groups is an anti-inflammatory agent.

16. The polymer conjugate of a physiologically active substance according to claim 15, in which the anti-inflammatory agent is a steroid anti-inflammatory agent.

17. The polymer conjugate of a physiologically active substance according to any one of claims 1, 2 or 3, in which the physiologically active substance having the one or more hydroxy groups is a pain relieving agent, a hair growing agent, or a myocardial protective agent having an effect of decreasing myocardial infarction size.

18. The polymer conjugate of a physiologically active substance according to claim 17, in which the pain relieving agent, hair growing agent, or myocardial protective agent having an effect of decreasing myocardial infarction size is adenosine.

19. The polymer conjugate of a physiologically active substance according to any one of claims 1, 2 or 3, characterized in that the polymer conjugate forms a micelle in water.

20. A pharmaceutical agent comprising the polymer conjugate of a physiologically active substance according to any one of claims 1, 2 or 3 as an effective component.

21. An anticancer agent comprising the polymer conjugate of a physiologically active substance according to any one of claims 4 to 14 as an active ingredient.

22. An anti-inflammatory agent comprising the polymer conjugate of a physiologically active substance according to claim 15 as an active ingredient.

* * * * *